United States Patent
Kim et al.

(10) Patent No.: US 12,009,106 B2
(45) Date of Patent: Jun. 11, 2024

(54) EMERGENCY DEMAND PREDICTION DEVICE, EMERGENCY DEMAND PREDICTION METHOD, AND PROGRAM

(71) Applicant: NIPPON TELEGRAPH AND TELEPHONE CORPORATION, Tokyo (JP)

(72) Inventors: Sunyong Kim, Musashino (JP); Ippei Shake, Musashino (JP); Kazuaki Obana, Musashino (JP); Atsuhiko Maeda, Musashino (JP); Michiharu Takemoto, Musashino (JP); Yukio Kikuya, Musashino (JP); Hiroshi Sato, Musashino (JP); Tetsuo Kawano, Musashino (JP); Kenichi Fukuda, Tokyo (JP)

(73) Assignee: NIPPON TELEGRAPH AND TELEPHONE CORPORATION, Tokyo (JP)

( * ) Notice: Subject to any disclaimer, the term of this patent is extended or adjusted under 35 U.S.C. 154(b) by 474 days.

(21) Appl. No.: 17/294,514

(22) PCT Filed: Nov. 8, 2019

(86) PCT No.: PCT/JP2019/043920
§ 371 (c)(1),
(2) Date: May 17, 2021

(87) PCT Pub. No.: WO2020/105478
PCT Pub. Date: May 28, 2020

(65) Prior Publication Data
US 2022/0020502 A1  Jan. 20, 2022

(30) Foreign Application Priority Data

Nov. 19, 2018 (JP) ................. 2018-216605

(51) Int. Cl.
*G16H 50/70* (2018.01)
*G16H 50/20* (2018.01)

(52) U.S. Cl.
CPC ............. *G16H 50/70* (2018.01); *G16H 50/20* (2018.01)

(58) Field of Classification Search
None
See application file for complete search history.

(56) References Cited

U.S. PATENT DOCUMENTS

| 2017/0161614 | A1* | 6/2017 | Mehta | G06N 20/00 |
| 2017/0364803 | A1* | 12/2017 | Calmon | G06N 3/045 |
| 2018/0053401 | A1* | 2/2018 | Martin | G07C 5/008 |

OTHER PUBLICATIONS

R. Aringhieri, M.E. Bruni, S. Khodaparasti, J.T. van Essen, Emergency medical services and beyond: Addressing new challenges through a wide literature review, Computers & Operations Research, vol. 78, 2017, pp. 349-368, ISSN 0305-0548, https://doi.org/10.1016/j.cor.2016.09.016. (Year: 2017).*

(Continued)

*Primary Examiner* — Devin C Hein
(74) *Attorney, Agent, or Firm* — Harness, Dickey & Pierce, P.L.C.

(57) ABSTRACT

Provided is a technique for efficiently predicting the number (quantity) of occurrences of emergency medical service requests in a target area. An emergency medical service demand prediction device according to an embodiment obtains actual history data including information about dates and times of occurrences of emergency medical service requests, information about positions of the occurrences of the emergency medical service requests, and information about illnesses and injuries that caused the emergency medical service requests; the device generates a first learning model that receives an input of first learning-purpose data generated on a basis of learning-purpose actual history (Continued)

data and outputs illness/injury groups; the device generates a second learning model that receives an input of second learning-purpose data generated on a basis of the learning-purpose actual history data and the illness/injury groups output from the first learning model and outputs a value indicating a quantity of occurrences of emergency medical service requests for each unit area; and the device predicts a quantity of occurrences of emergency medical service requests in each unit area, by inputting, to the second learning model having been trained, prediction-purpose data generated on a basis of prediction-purpose actual history data and the illness/injury groups output from the first learning model having been trained.

19 Claims, 22 Drawing Sheets

(56) References Cited

OTHER PUBLICATIONS

A. Micheletti, D. Morale, D. Rapati and P. Nolli, "A stochastic model for simulation and forecasting of emergencies in the area of Milano," 2010 IEEE Workshop on Health Care Management (WHCM), Venice, Italy, 2010, pp. 1-6, doi: 10.1109/WHCM.2010.5441259. (Year: 2010).*

Study group on proper placement of ambulance crews (Sapporo City Fire Department), Research on proper placement of paramedics due to increased emergency demand, 2014 General Incorporated Foundation Emergency Promotion Foundation Research and Research Grant Program, Mar. 2015.

Efficient placement of ambulances Utilization of big data, demand forecast, Nihon Keizai Shimbun electronic version, Oct. 28, 2016, https://www.nikkei.com/article/DGXLASFS31H0P_Y6A021C1MM0000/.

* cited by examiner

Fig. 5

| ID | DATE/TIME OF OCCURRENCE | DISPATCH AREA | AGE GROUP (10-YEAR INCREMENTS) | GENDER | PLACE OF OCCURRENCE | TYPE OF ILLNESS/INJURY | BODY PART OF ILLNESS/INJURY | DEGREE OF ILLNESS/INJURY | ... |
|---|---|---|---|---|---|---|---|---|---|
| 1 | 2018/8/2 10:23:45 | 2 CHOME, XX TOWN | 50 | FEMALE | GENERAL HOUSING | DIZZINESS | | MINOR | |
| 2 | 2018/8/2 10:42:14 | 1 CHOME, ** TOWN | 30 | MALE | HOUSING COMPLEX | HEATSTROKE | | SERIOUS | |
| 3 | 2018/8/2 10:48:42 | INTERSECTION NEAR Y STATION | 10 | MALE | ON A STREET | FRACTURE | FOOT | MEDIUM | |
| 4 | 2018/8/2 11:02:39 | BLOCK *X, ZZ DISTRICT | 80 | FEMALE | GENERAL HOUSING | LUMBAGO | LUMBUS | MEDIUM | |
| 5 | 2018/8/2 11:04:53 | 1 CHOME, XX TOWN | 70 | MALE | NURSING HOME | CEREBRAL INFARCTION | | SERIOUS | |

Fig. 6A

| NAMES OF ILLNESSES | g1 | g2 | g3 | g4 | g5 | g6 | .... |
|---|---|---|---|---|---|---|---|
| OTHER MALIGNANT NEOPLASMS | 6 | 12 | 11 | 15 | 7 | 12 | |
| DIABETES | 3 | 7 | 4 | 5 | 3 | 7 | |
| OTHER DISORDERS OF ENDOCRINE SYSTEM, ETC. | 31 | 45 | 47 | 55 | 19 | 66 | |
| ANEMIA | 4 | 2 | 5 | 8 | 2 | 7 | |
| HYPERVENTILATION SYNDROME | 51 | 45 | 35 | 42 | 16 | 26 | |
| BOUT OF SYNCOPE | 78 | 68 | 92 | 77 | 22 | 125 | |
| HYPERTENSION | 9 | 17 | 14 | 8 | 7 | 17 | |
| PERIPHERAL NERVOUS SYSTEM DISORDERS | 5 | 6 | 10 | 4 | 6 | 9 | |
| OTHER CENTRAL NERVOUS SYSTEM DISEASES | 6 | 10 | 12 | 16 | 4 | 11 | |
| ISCHEMIC DISEASES | 53 | 76 | 55 | 73 | 50 | 82 | |
| OTHER CARDIAC DISEASES | 73 | 110 | 152 | 148 | 96 | 155 | |
| CEREBRAL HEMORRHAGE | 44 | 51 | 62 | 69 | 29 | 91 | |
| CEREBRAL INFARCTION | 56 | 116 | 108 | 103 | 61 | 128 | |
| OTHER CEREBROVASCULAR DISEASES | 36 | 47 | 37 | 40 | 32 | 42 | |
| OTHER CIRCULATORY SYSTEM DISEASES | 17 | 32 | 23 | 36 | 18 | 42 | |
| ACUTE UPPER RESPIRATORY TRACT INFECTION | 11 | 18 | 14 | 12 | 14 | 28 | |
| ACUTE BRONCHITIS | 1 | 3 | 1 | 4 | 5 | 5 | |
| PNEUMONIA | 69 | 148 | 135 | 139 | 55 | 142 | |
| ASTHMA | 3 | 13 | 14 | 15 | 20 | 22 | |
| INFLUENZA | 22 | | 14 | 6 | 6 | 39 | |
| ... | | | | | | | |

| | | | | | | |
|---|---|---|---|---|---|---|
| □ | A1 | FEBRILE CONVULSION | ○ | E2 | OTHER DRUG POISONING | ● | G9 | FRACTURE OF RIB/STERNUM, CLOSED |
| □ | A2 | HYPERVENTILATION SYNDROME | ○ | F1 | OTHER DIGESTIVE DISEASES | ● | G10 | FRACTURE OF CERVICAL/THORACIC/LUMBAR VERTEBRAE, CLOSED |
| □ | A3 | FOREIGN SUBSTANCE IN MOUTH/ESOPHAGUS/STOMACH | ○ | F2 | OTHER CENTRAL NERVOUS SYSTEM DISEASES | ● | G11 | OTHER CARDIAC DISEASES |
| ■ | B1 | NAUSEA, VOMITING, ETC. | ○ | F3 | BOWEL OBSTRUCTION, HERNIA | ✱ | H1 | FOREIGN SUBSTANCE IN PHARYNX/LARYNX |
| ■ | B2 | APPENDICITIS | ○ | F4 | HEMATEMESIS, MELENA | ✱ | H2 | OTHER INFECTIOUS DISEASES, ETC. |
| ■ | B3 | ACUTE ALCOHOLISM | ○ | F5 | CEREBRAL INFARCTION | ✱ | H3 | ANEMIA |
| ■ | B4 | ISCHEMIC DISEASES | ○ | F6 | CEREBRAL HEMORRHAGE | ✱ | H4 | HYPERTENSION |
| ■ | B5 | UPPER LIMB OPEN WOUND | ○ | F7 | OTHER CEREBROVASCULAR DISEASES | ☆ | I1 | UPPER LIMB CONTUSION HEMATOMA |
| ■ | B6 | Nan | ○ | F8 | SYMPTOMS UNCLEAR | ☆ | I2 | LOWER LIMB SCRAPE WOUND |
| ■ | B7 | PERIPHERAL NERVOUS SYSTEM DISORDERS | ○ | F9 | CHOLELITHIASIS, CHOLECYSTITIS | ☆ | I3 | TRUNK CONTUSION HEMATOMA |
| ■ | B8 | OTHER UROLOGICAL DISEASES | ○ | F10 | OTHER DISORDERS OF ENDOCRINE SYSTEM, ETC. | ☆ | I4 | WHOLE BODY CONTUSION |
| ▲ | C1 | ACUTE UPPER RESPIRATORY TRACT INFECTION | ○ | F11 | OTHER LIVER DISEASES | ☆ | I5 | FRACTURE OF CLAVICLE/SCAPULAR, CLOSED |
| ▲ | C2 | HEADACHE | ○ | F12 | PNEUMONIA | ☆ | I6 | LOWER LIMB CONTUSION HEMATOMA |
| ▲ | C3 | GASTRITIS, DUODENITIS | ○ | F13 | OTHER CIRCULATORY SYSTEM DISEASES | ☆ | I7 | JAW DISLOCATION/SPRAIN |
| ▲ | C4 | CHEST PAIN, DYSPNEA, ETC. | ● | G1 | STOMACH/DUODENAL ULCER | ☆ | I8 | CONTUSION OF FACE, HEAD, OR JAW |
| ▲ | C5 | CONCURRENT SYMPTOMS OF HEART | ● | G2 | LUMBAGO | ◎ | J1 | DISEASE IN FEMALE GENITALIA, ETC. |
| ▲ | C6 | ABDOMINAL PAIN | ● | G3 | OTHER RESPIRATORY SYSTEM DISEASES | ◎ | J2 | COMPLICATIONS FROM PREGNANCY, DELIVERY, ETC. |
| ▲ | C7 | ACUTE BRONCHITIS | ● | G4 | OTHER MALIGNANT NEOPLASMS | ◎ | J3 | OTHERS |
| ▲ | C8 | SHOULDER DISLOCATION/SPRAIN | ● | G5 | DIABETES | ● | K1 | OPEN WOUND IN JAW/FACE |
| ▲ | C9 | UROLOGICAL CALCULI | ● | G6 | OTHER SPINAL DISEASES | ● | K2 | DISLOCATION/SPRAIN OF TOE/FINGER |
| △ | D1 | OTHER TYPES OF SHOCK | ● | G7 | BRONCHOPULMONARY MALIGNANT NEOPLASMS | × | L1 | INFLUENZA |
| ○ | E1 | SEDATIVE/HYPNOTIC POISONING | ● | G8 | RENAL FAILURE | | | |

1 CHOME, ** TOWN

| DATE/TIME | ILLNESS/INJURY GROUP 1 | ILLNESS/INJURY GROUP 2 | ILLNESS/INJURY GROUP 3 | ILLNESS/INJURY GROUP 4 | ILLNESS/INJURY GROUP 5 | ... | TOTAL NUMBER OF OCCURRENCES |
|---|---|---|---|---|---|---|---|
| 2018/8/2 10:00 | 2 | 0 | 1 | 2 | 0 | | 12 |
| 2018/8/2 11:00 | 0 | 2 | 0 | 3 | 0 | | 14 |
| 2018/8/2 12:00 | 1 | 1 | 0 | 2 | 0 | | 7 |
| 2018/8/2 13:00 | 0 | 2 | 0 | 5 | 1 | | 13 |
| 2018/8/2 14:00 | 0 | 0 | 3 | 1 | 0 | | 8 |

Fig. 8

| DATE/TIME | AREA | PREDICTED VALUE | ACTUAL COUNTED VALUE |
|---|---|---|---|
| 2018/8/2 10:00 | 1 CHOME, ** TOWN | 18 | |
| 2018/8/2 10:00 | 2 CHOME, ** TOWN | 12 | |
| 2018/8/2 10:00 | 1 CHOME, XX TOWN | 4 | |
| ... | | | |
| 2018/8/2 11:00 | 1 CHOME, ** TOWN | 14 | |

Fig. 10

| YEAR/MONTH/DATE/TIME | TEMPERATURE (°C) | TEMPERATURE (°C) CONDITION 1 | TEMPERATURE (°C) CONDITION 2 | PRECIPITATION (mm) | PRECIPITATION (mm) CONDITION 3 | PRECIPITATION (mm) CONDITION 1 | PRECIPITATION (mm) CONDITION 2 | SNOWFALL (cm) | SNOWFALL (cm) CONDITION 3 | SNOWFALL (cm) CONDITION 1 | SNOWFALL (cm) CONDITION 2 | HOURS OF SUNLIGHT (HOURS) | HOURS OF SUNLIGHT (HOURS) CONDITION 3 | ... |
|---|---|---|---|---|---|---|---|---|---|---|---|---|---|---|
| 2018/8/2 10:00 | 28.3 | 8 | 1 | 0 | 1 | 8 | 1 | | | 1 | 1 | 0 | 0 | |
| 2018/8/2 11:00 | 30 | 8 | 1 | 0 | 1 | 8 | 1 | | | 1 | 1 | 0.9 | 0 | |
| 2018/8/2 12:00 | 31.7 | 8 | 1 | 0 | 1 | 8 | 1 | | | 1 | 1 | 1 | 0 | |
| 2018/8/2 13:00 | 31.4 | 8 | 1 | 0 | 1 | 8 | 1 | | | 1 | 1 | 0.1 | 0 | |
| 2018/8/2 14:00 | 31.4 | 8 | 1 | 0 | 1 | 8 | 1 | | | 1 | 1 | 0.3 | 0 | |

Fig. 11

| YEAR/MONTH/DATE/TIME | TEMPER-ATURE | PRECIP-ITATION | PRECIP-ITATION CONDITION 3 | SNOW-FALL | SNOW-FALL CONDITION 3 | HOURS OF SUNLIGHT | HOURS OF SUNLIGHT CONDITION 3 | SNOW ACCUMU-LATION | SNOW ACCUMU-LATION CONDITION 3 | WIND SPEED | INSO-LATION | ATMOS-PHERIC PRESSURE | ... |
|---|---|---|---|---|---|---|---|---|---|---|---|---|---|
| 2018/8/2 10:00 | 0.814 | 0 | 1 | 0 | 1 | 0 | 0 | 0 | 1 | 0.14 | 0.06 | 0.465 | |
| 2018/8/2 11:00 | 0.852 | 0 | 1 | 0 | 1 | 0.9 | 0 | 0 | 1 | 0.01 | 0.18 | 0.472 | |
| 2018/8/2 12:00 | 0.877 | 0 | 1 | 0 | 1 | 1 | 0 | 0 | 1 | 0.04 | 0.88 | 0.468 | |
| 2018/8/2 13:00 | 0.892 | 0 | 1 | 0 | 1 | 0.1 | 0 | 0 | 1 | 0.12 | 0.89 | 0.464 | |
| 2018/8/2 14:00 | 0.894 | 0 | 1 | 0 | 1 | 0.3 | 0 | 0 | 1 | 0.13 | 0.92 | 0.463 | |

Fig. 13

| | POPULATION: MALE | POPULATION: FEMALE | AGE 0-9 | AGE 10-19 | AGE 20-29 | AGE 30-39 | AGE 40-49 | AGE 50-59 | AGE 60-69 | AGE 70 OR OLDER | AGE UNKNOWN | AGE 0-14 | AGE 15-64 | AGE 65 OR OLDER |
|---|---|---|---|---|---|---|---|---|---|---|---|---|---|---|
| 2018/8/2 10:00 | 250 | 261 | 37 | 52 | 65 | 60 | 58 | 73 | 76 | 90 | 0 | 60 | 328 | 123 |
| 2018/8/2 11:00 | 268 | 265 | 27 | 46 | 76 | 68 | 62 | 88 | 64 | 102 | 0 | 46 | 358 | 129 |
| 2018/8/2 12:00 | 549 | 574 | 104 | 106 | 140 | 166 | 120 | 165 | 134 | 187 | 1 | 146 | 729 | 247 |
| 2018/8/2 13:00 | 599 | 634 | 78 | 75 | 197 | 208 | 129 | 185 | 155 | 206 | 0 | 105 | 845 | 283 |
| 2018/8/2 14:00 | 630 | 611 | 44 | 84 | 251 | 189 | 146 | 184 | 152 | 191 | 0 | 78 | 892 | 271 |

Fig. 15

| DATE/TIME | POPULATION: MALE | POPULATION: FEMALE | AGE 0-9 | AGE 10-19 | ... | HOSPITALS | CLINICS | NURSING HOMES | ELEMENTARY SCHOOLS | JUNIOR HIGH SCHOOLS | ... |
|---|---|---|---|---|---|---|---|---|---|---|---|
| 2018/8/2 10:00 | 250 | 261 | 37 | 52 | | 1 | 0 | 2 | 0 | 1 | |
| 2018/8/2 11:00 | 268 | 265 | 27 | 46 | | 1 | 0 | 2 | 0 | 1 | |
| 2018/8/2 12:00 | 549 | 574 | 104 | 106 | | 1 | 0 | 2 | 0 | 1 | |
| 2018/8/2 13:00 | 599 | 634 | 78 | 75 | | 1 | 0 | 2 | 0 | 1 | |
| 2018/8/2 14:00 | 630 | 611 | 44 | 84 | | 1 | 0 | 2 | 0 | 1 | |

Fig. 16

| AREA | BUSINESS DISTRICT | COMMERCIAL DISTRICT | SCHOOL DISTRICT (UNIVERSITY) | SCHOOL DISTRICT (ELEMENTARY, JUNIOR AND SENIOR HIGH) | HOSPITALS | PARKS/ SPORTS | RESIDENTIAL AREA (MATURE) | RESIDENTIAL AREA (NEWLY DEVELOPED) | ... |
|---|---|---|---|---|---|---|---|---|---|
| 1 CHOME, ** TOWN | 0 | 0 | 0 | 1 | 0 | 0 | 1 | 0 | |
| 2 CHOME, ** TOWN | 0 | 1 | 1 | 0 | 1 | 1 | 1 | 0 | |
| 1 CHOME, XX TOWN | 1 | 1 | 0 | 0 | 0 | 0 | 0 | 0 | |
| 1 CHOME, ** TOWN | 0 | 0 | 1 | 0 | 0 | 1 | 0 | 1 | |

Fig. 19

| DATE/TIME | COLD | HEADACHE | DIZZINESS | HEAT-STROKE | CEREBRAL INFARCTION | FRACTURE OF HAND | FRACTURE OF FOOT | ... | TOTAL NUMBER OF OCCURRENCES |
|---|---|---|---|---|---|---|---|---|---|
| 2018/8/2 10:00 | 2 | 0 | 1 | 2 | 0 | 0 | 0 | | 12 |
| 2018/8/2 11:00 | 0 | 2 | 0 | 3 | 0 | 0 | 0 | | 14 |
| 2018/8/2 12:00 | 1 | 1 | 0 | 2 | 0 | 0 | 0 | | 7 |
| 2018/8/2 13:00 | 0 | 2 | 0 | 5 | 1 | 0 | 0 | | 13 |
| 2018/8/2 14:00 | 0 | 0 | 3 | 1 | 0 | 1 | 0 | | 8 |

# EMERGENCY DEMAND PREDICTION DEVICE, EMERGENCY DEMAND PREDICTION METHOD, AND PROGRAM

CROSS-REFERENCE TO RELATED APPLICATIONS

This application is a 371 U.S. National Phase of International Application No. PCT/JP2019/043920 filed on Nov. 8, 2019, which claims priority to Japanese Application No. 2018-216605 filed on Nov. 19, 2018. The entire disclosures of the above applications are incorporated herein by reference.

TECHNICAL FIELD

An aspect of the present invention relates to an emergency medical service demand prediction device, an emergency medical service demand prediction method, and a program for predicting the number of occurrences of emergency medical service requests in emergency medicine.

BACKGROUND ART

Along with the population aging of recent years, the number of emergency medical staff dispatches triggered by the 119 calls from citizens in Japan is increasing year by year. In addition, working periods of the dispatched emergency medical staff also have a tendency of increasing. In actual paramedic situations, a delay of a few minutes can be fatal. However, because a budget allocated to the fire stations is limited, the number of emergency medical staff is not expected to increase significantly. It is therefore an urgent task to develop a technique for reducing the working periods of the dispatched emergency medical staff.

For example, in the City of Sapporo, an attempt has been made to predict the demand for emergency medical services in the future for each municipal ward, by multiplying a predicted future increase in the population by the numbers of emergency medical transports in different municipal wards (Central Ward, North Ward, East Ward, etc.) and age groups in five-year increments (ages 0-4, 5-9, 10-14, and so on), so as to explore an optimal allocation of ambulances (Non-Patent Literature 1). Further, the Japanese Ministry of Internal Affairs and Communications publicized introducing a system related to a prediction of the demand for emergency medical services made by using big data and to efficient allocations of ambulances based on the prediction (Non-Patent Literature 2).

CITATION LIST

Non-Patent Literature

Non-Patent Literature 1: Kyukyutai no Tekisei Haichi Nado ni Kansuru Kenkyukai (Sapporo Shi Shobokyoku), Heisei 26 Nendo Ippan Zaidan Hojin Kyukyu Shinko Zaidan Chosa Kenkyu Josei Jigyo "Kyukyu Juyo Zoka ni Tomonau Kyukyutai no Tekisei Haichi Nado ni Kansuru Kenkyu ni Tsuite" [A Study Group on an Optimal Allocation of Emergency Medical Staff and others (The Fire Department of The City of Sapporo) A 2014 Research Subsidy Program of the General Incorporated Foundation, Foundation for Ambulance Service Development, "A Study on an Optimal Allocation of Emergency Medical Staff and Others in Response to an Increase in the Demand for Emergency Medical Services" (in Japanese)], [online], March 2015, Internet <URL: http://www.fasd.or.jp/tyousa/pdf/h26tekisei.pdf>

Non-Patent Literature 2: The Nikkei Newspaper, Electronic Edition, "Kyukyusha o Koritsu Haichi, Big Data Katsuyo, Juyo Yosoku" [Efficient Allocation of Ambulances, Utilizing Big Data to Predict the Demand (in Japanese)] [online], Oct. 28, 2016, Internet <URL: https://www.nikkei.com/article/DGXLASFS31HOP_Y6A021C1MM00 00/>

SUMMARY OF THE INVENTION

Technical Problem

According to the techniques described in the listed non-patent literature, in order to optimally allocate the ambulances, it is necessary to predict the demand for emergency medical services on the level of small regions (e.g., the Japanese 'chome' (address blocks) or tertiary meshes). However, as the region is divided into small sections, the frequency of occurrences of emergency medical service requests also decreases. It is therefore extremely difficult to analyze the occurrences as probability events.

In this regard, the number of occurrences of emergency medical service requests is considered to be impacted by various environmental factors. Examples of the environmental factors include the following:

Climate information such as temperature, humidity, atmospheric pressure, and the like (heatstroke, migraine, asthma, arthralgia, etc.)

Weather information (traffic accidents due to rainfalls, people slipping on snow-covered ground, etc.)

epidemic situations of infectious diseases (colds, influenza, etc.)

characteristics unique to certain regions (acute alcoholism in commercial districts, etc.).

It is considered possible to enhance the precision of an estimation of the demand for emergency medical services, by making clear the various environmental factors and groups of illnesses and injuries impacted by those factors. In emergency medical transport data, however, because the types of illnesses and injuries are categorized in extremely small divisions, generally speaking, many illnesses and injuries do not exhibit sufficiently high frequency of occurrences that withstand analyses. Further, different municipalities use different formats for emergency medical transport data. Also, different municipalities use different categorizations of illnesses and injuries. It is therefore not easy to generalize the information.

In view of the circumstances described above, it is an object of the present invention to provide a technique for predicting the number of occurrences of emergency medical service requests efficiently with a high level of precision.

Means for Solving the Problem

To solve the problem described above, a first aspect of the present invention provides: an emergency medical service demand prediction device that predicts a quantity of occurrences of emergency medical service requests in a target area, the emergency medical service demand prediction device including: an actual history data obtainment unit that obtains actual history data including date/time information indicating dates and times of occurrences of emergency medical service requests, position information indicating places of the occurrences of the emergency medical service requests, and illness/injury information indicating illnesses and injuries that caused the emergency medical service requests; a first learning unit that generates a first learning model which receives an input of first learning-purpose data generated on a basis of the actual history data obtained for a learning purpose and outputs illness/injury groups to which the illnesses and injuries indicated in the actual history data as having caused the emergency medical service requests belong; a second learning unit that generates a second learning model which receives an input of second learning-purpose data generated on a basis of the actual history data obtained for the learning purpose and the illness/injury groups output from the first learning model and outputs a value indicating a quantity of occurrences of emergency medical service requests; and a request occurrence number prediction unit that predicts a quantity of occurrences of emergency medical service requests in each unit area within the target area, by inputting, to the second learning model having been trained, prediction-purpose data generated on a basis of the actual history data obtained for a prediction purpose and the illness/injury groups output from the first learning model having been trained.

A second aspect of the present invention is obtained by configuring the first aspect so as to further include: an environment data obtainment unit that, on a basis of the position information included in the actual history data, obtains environment data including information related to meteorology of the places of the occurrences of the emergency medical service requests, and configuring so that the second learning unit generates the second learning model by further receiving an input of the environment data obtained for a learning purpose; and so that the request occurrence number prediction unit predicts the quantity of the occurrences of the emergency medical service requests for each unit area, by further inputting the environment data obtained for a prediction purpose to the second learning model having been trained.

A third aspect of the present invention is obtained by configuring the first aspect so as to further include: a region data obtainment unit that, on a basis of the position information included in the actual history data, obtains region data including information related to a regional statistic of the places of the occurrences of the emergency medical service requests, and configuring so that the second learning unit generates the second learning model by further receiving an input of the region data obtained for a learning purpose; and so that the request occurrence number prediction unit predicts the quantity of the occurrences of the emergency medical service requests for each unit area, by further inputting the region data obtained for a prediction purpose to the second learning model having been trained.

A fourth aspect of the present invention is obtained by configuring the first aspect so as to further include: a region data obtainment unit that, on a basis of the position information included in the actual history data, obtains region data including information related to a regional statistic of the places of the occurrences of the emergency medical service requests; and a third learning unit that generates a third learning model which receives an input of the region data obtained for a learning purpose and outputs a regional feature value for each unit area, and so that the second learning unit generates the second learning model by further receiving an input of the regional feature value output from the third learning model; and so that the request occurrence number prediction unit predicts the quantity of the occurrences of the emergency medical service requests for each unit area by further inputting the regional feature value output from the third learning model having been trained, to the second learning model having been trained.

A fifth aspect of the present invention is obtained by configuring the first aspect so that the first learning model is structured by using a first layer of a neural network; and so that the second learning model is structured by using a second layer of the neural network that receives an output of the first layer as an input.

A sixth aspect of the present invention is obtained by configuring any one of the first to the fifth aspects so as to further include: a prediction result output unit that generates and outputs output data for visually presenting a prediction result obtained by the request occurrence number prediction unit.

Effects of the Invention

According to the first aspect of the present invention, on the basis of the actual history data related to the occurrences of the emergency medical service requests and including the date/time information, the position information, and the information about the illnesses and injuries that caused the emergency medical service requests, the first learning-purpose data is generated, at first, from the actual history data obtained for the learning purpose. The learning process is performed with the first model that receives the input of the first learning-purpose data and outputs the illness/injury groups to which the illnesses and injuries belong. Subsequently, the second learning-purpose data is generated on the basis of the actual history data obtained for the learning purpose and the illness/injury groups output from the first model. The learning process is performed with the second model that receives the input of the second learning-purpose data and outputs the value indicating the quantity of the occurrences of the emergency medical service requests. The quantity of the occurrences (hereinafter, "the number of occurrences") of the emergency medical service requests for each unit area is predicted by using the trained first and second models obtained in this manner and the actual history data obtained for the predicting purpose.

With these arrangements, even when the obtained actual history data of the emergency medical transports do not have sufficiently high frequency of occurrences that can withstand analyses in units of illnesses and injuries, the categorization of the illnesses and injuries is at first learned on the basis of the actual history data, so that the result of the categorization is reflected on the actual history data and used in the analyses. It is therefore possible to predict the number of occurrences of the emergency medical service requests with an excellent level of precision while efficiently utilizing the limited actual history data. Further, the actual history data reflecting the result of the categorization is used in the learning process of the prediction model. It is therefore also possible to absorb the differences among the municipalities in the categorization of the illnesses and injuries and to thus easily construct the models that can be used in common among a plurality of municipalities.

According to the second aspect of the present invention, the environment data including the information related to meteorology of the places of occurrences of the emergency medical service requests is obtained, so that the obtained environment data is further used in the learning and predicting processes. With this arrangement, it is possible to perform the learning process having a high reliability by keeping the actual history of the occurrences of the emergency medical service requests in association with the information related to meteorology of the regions. It is therefore also possible to predict the number of occurrences of the emergency medical service requests in the regions with a high level of precision.

According to the third aspect of the present invention, the region data including the information related to the regional statistics of the places of occurrences of the emergency medical service requests is obtained, so that the obtained region data is further used in the learning and predicting processes. With this arrangement, it is possible to perform the learning process having a high reliability by keeping the actual history of the occurrences of the emergency medical service requests in association with the information related to the regional statistics of the regions. It is therefore also possible to predict the number of occurrences of the emergency medical service requests in the regions with a high level of precision.

According to the fourth aspect of the present invention, the region data including the information related to the regional statistics of the places of occurrences of the emergency medical service requests is obtained. On the basis of the obtained region data, the regional feature value is extracted for each unit area, so that the extracted regional feature values are further used in the learning and predicting processes. With this arrangement, it is possible to perform the learning process having a high reliability by keeping the actual history of the occurrences of the emergency medical service requests in association with the feature values related to the regional statistic information unique to each region. Further, it is therefore also possible to predict the number of occurrences of the emergency medical service requests in the regions with a high level of precision.

According to the fifth aspect of the present invention, the first learning model is structured by using the first layer of the neural network, whereas the output of the first layer is input to the second learning model represented by the second layer of the neural network. With this arrangement, without the need to perform separate processes, it is possible to collectively perform the learning, updating, and predicting processes of the two learning models, by inputting the actual history data to the neural network.

According to the sixth aspect of the present invention, the prediction result of the number of occurrences of the emergency medical service requests is output as the output data for visually presenting the prediction result. With this arrangement, it is possible to easily understand the number of occurrences of the emergency medical service requests for each unit area that is predicted for the near future. It is therefore possible to promptly take appropriate measures.

In other words, according to the aspects of the present invention, it is possible to provide a technique for predicting the number of occurrences of the emergency medical service requests efficiently with a high level of precision.

BRIEF DESCRIPTION OF DRAWINGS

FIG. 5 is a table showing an example of actual history data of emergency medical transports.

FIG. 6A is a table showing an example of a result of extracting illness/injury groups by using a clustering scheme.

FIG. 6C is a table showing descriptions of the markers in FIG. 6B.

FIG. 7 is a table showing an example of prediction model learning-purpose data.

FIG. 8 is a table showing an example of a prediction result obtained by the emergency medical service demand prediction device shown in FIG. 1.

FIG. 10 is a table showing an example of environment data.

FIG. 11 is a table showing an example of environment data on which pre-processing processes have been performed.

FIG. 13 is a table showing an example of region data.

FIG. 15 is a table showing an example of regional characteristic learning-purpose data.

FIG. 16 is a table showing an example of regional characteristic learning results.

FIG. 19 is a table showing an example of learning-purpose data used in the learning procedure shown in FIG. 17.

DESCRIPTION OF EMBODIMENTS

The following will describe embodiments of the present invention, with reference to the drawings.

Exemplary Embodiments

First Embodiment Example

<A Configuration>

Figure 1:
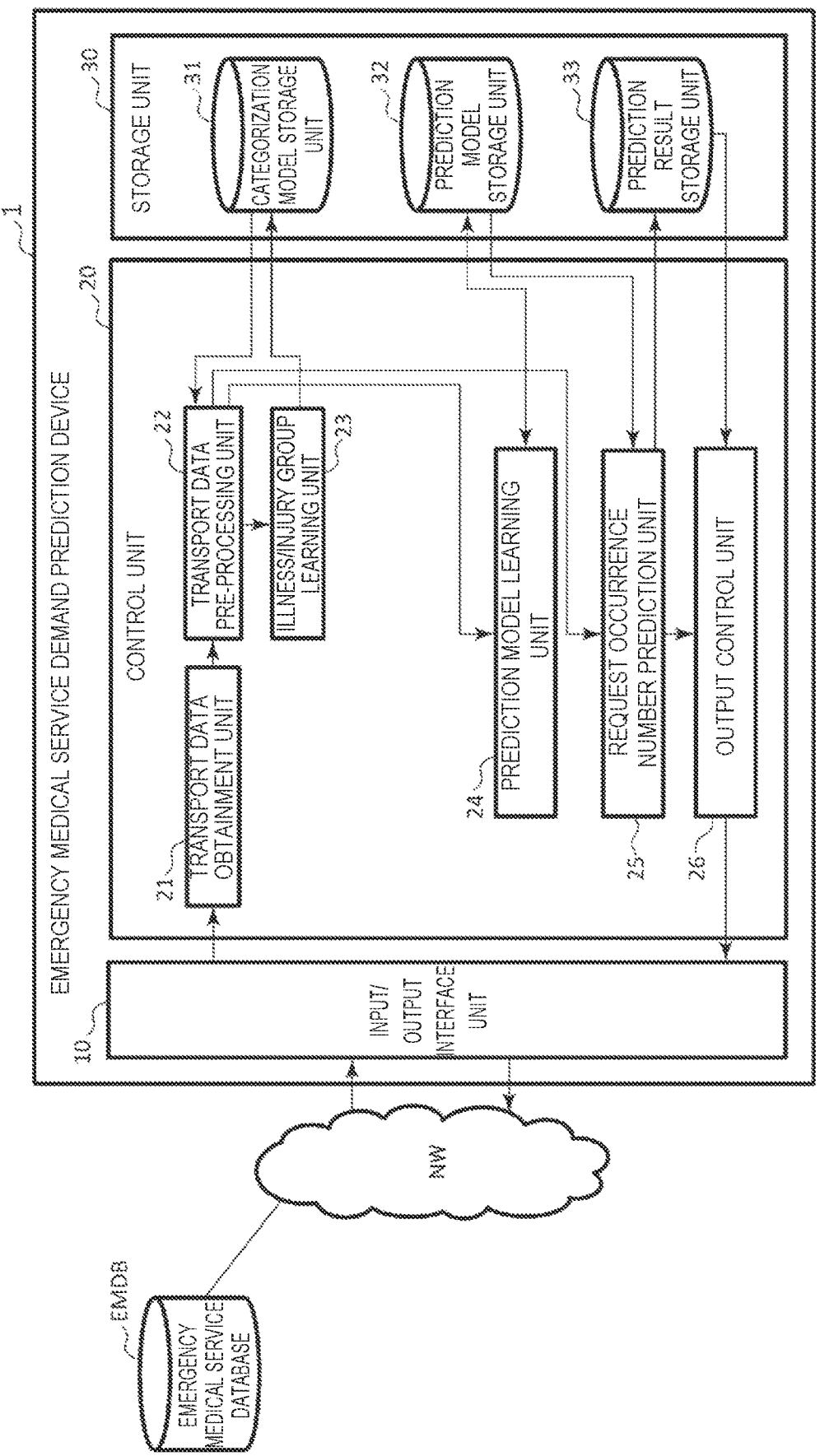
FIG. 1 is a block diagram showing a first example of a functional configuration of an emergency medical service demand prediction device according to an embodiment of the present invention.

FIG. 1 is a block diagram showing a functional configuration of an emergency medical service demand prediction device 1 according to an embodiment of the present invention.

The emergency medical service demand prediction device 1 is managed by the fire department headquarter of each municipality, for example, and is configured to estimate the number of occurrences of emergency medical service per unit time period per unit area, for a number of hours or days later, by using the number of occurrences of emergency medical service requests per unit area in the past as training data. The emergency medical service demand prediction device 1 may be configured by using a server computer or a personal computer, for example.

The emergency medical service demand prediction device 1 is capable of communicating with various types of servers and databases such as an emergency medical service database EMDB, via a network NW. For example, the emergency medical service database EMDB has accumulated therein data related to an actual history of occurrences of emergency medical service requests, including emergency medical transport information and patient information input by control offices and emergency medical staff.

The network NW is structured with, for example, a relay network and a plurality of access networks for accessing the relay network. Examples include public networks such as the Internet being commonly used and closed networks that are controlled so that only limited devices can have access thereto. As the relay network, for example, a public network or a closed network using an internet protocol may be used. As the access networks, for example, Local Area Networks (LANs), wireless LANs, mobile phone networks, wired phone networks, Fiber To The Home (FTTH) systems, or Cable Television (CATV) networks, may be used.

The emergency medical service demand prediction device 1 according to an embodiment includes an input/output interface unit 10, a control unit 20, and a storage unit 30.

The input/output interface unit 10 includes, for example, at least one wired or wireless communication interface unit and makes it possible to transmit and receive information to and from external devices. Examples of the wired interface include a wired LAN. Examples of the wireless interface include an interface using a low-power wireless data communication standard such as a wireless LAN or Bluetooth (registered trademark).

For example, under control of the control unit 20, the input/output interface unit 10 performs a process of accessing the emergency medical service database EMDB, reading any of the accumulated data, and further forwarding the read data to the control unit 20. Further, the input/output interface unit 10 is also capable of performing a process of outputting instruction information input through an input device (not shown) such as a keyboard, to the control unit 20. Further, the input/output interface unit 10 is capable of performing a process of outputting a learning result and a prediction result output from the control unit 20 to a display device (not shown) such as a liquid crystal display device or transmitting those results to an external device via the network NW.

The storage unit 30 uses, as a storage medium thereof, a non-volatile memory such as a Hard Disk Drive (HDD) or a Solid State Drive (SSD), for example, to and from which it is possible to write and read data when necessary. Further, as storage areas necessary for realizing the present embodiment, the storage unit 30 includes, in addition to a program storage unit, a categorization model storage unit 31, a prediction model storage unit 32, and a prediction result storage unit 33.

The categorization model storage unit 31 is used for storing therein a categorization model for re-categorizing illness/injury categories into groups of illnesses and injuries (hereinafter "illness/injury groups") on the basis of occurrence patterns.

The prediction model storage unit 32 is used for storing therein a prediction model for predicting the number of occurrences of emergency medical service requests in the future on the basis of actual history data from the past.

The prediction result storage unit 33 is used for storing therein a prediction result obtained by using the prediction model that has been trained (hereinafter, "trained prediction model").

It should be noted, however, that the storage units 31 to 33 are not requisite configurations and may be provided, for example, in an external storage medium such as a USB memory or in a storage device such as a database server placed in a cloud.

The control unit 20 includes (not shown) a hardware processor such as a Central Processing Unit (CPU) or a Micro Processing Unit (MPU) and a memory such as a Dynamic Random Access Memory (DRAM) or a Static Random Access Memory (SRAM). Further, the control unit 20 includes, as processing functions necessary for carrying out the present embodiment, a transport data obtainment unit 21, a transport data pre-processing unit 22, an illness/injury group learning unit 23, a prediction model learning unit 24, a request occurrence number prediction unit 25, and an output control unit 26. All of these processing functions are realized as a result of causing the abovementioned processor to execute a program stored in the storage unit 30. Alternatively, the control unit 20 may be realized in any of other various forms including an integrated circuit such as an Application Specific Integrated Circuit (ASIC) or a Field Programmable Gate Array (FPGA).

The transport data obtainment unit 21 functions as the actual history data obtainment unit and performs a process of obtaining, from the external emergency medical service database EMDB via the input/output interface unit 10, actual history data of emergency medical transports (hereinafter, "transport data") from the past that was recorded every time emergency medical staff was dispatched and further forwarding the obtained data to the transport data pre-processing unit 22.

The transport data pre-processing unit 22 performs a process of performing a pre-processing process on the received transport data and subsequently forwarding the resulting data to one selected from among the illness/injury group learning unit 23, the prediction model learning unit 24, and the request occurrence number prediction unit 25. For example, on the basis of the received transport data, the transport data pre-processing unit 22 generates one of illness/injury group learning-purpose data, prediction model learning-purpose data, or request occurrence number prediction-purpose data, by dividing the received data into sections, extracting necessary items, supplementing missing information, and performing a normalization process and further forwards the generated data to the units 23 to 25.

The illness/injury group learning unit 23 functions as the first learning unit and performs a process of receiving the illness/injury group learning-purpose data from the transport data pre-processing unit 22, further learning illness/injury groups each exhibiting similar occurrence patterns, and saving the learning result into the categorization model storage unit 31.

The prediction model learning unit 24 functions as the second learning unit and performs a process of receiving the prediction model learning-purpose data from the transport data pre-processing unit 22, further learning the prediction model for predicting the total number of occurrences of emergency medical service requests on the basis of the number of occurrences and date/time information of each illness/injury group, and saving the learning result into the prediction model storage unit 32.

The request occurrence number prediction unit 25 performs a process of predicting the number of occurrences of emergency medical service requests for each unit area, by receiving the request occurrence number prediction-purpose data from the transport data pre-processing unit 22, further reading the trained prediction model saved in the prediction model storage unit 32, and inputting the request occurrence number prediction-purpose data to the prediction model. Further, the request occurrence number prediction unit 25 performs a process of saving the prediction result into the prediction result storage unit 33.

The output control unit 26 performs a process of generating output data on the basis of the prediction result from the request occurrence number prediction unit 25 and further outputting the output data via the input/output interface unit 10. For example, the output control unit 26 is capable of generating the output data for causing a display device (not shown) to display the prediction number for each unit area as a two-dimensional map and outputting the generated output data to the display device. Also, the output control unit 26 is capable of generating the output data on the basis of the data stored in the categorization model storage unit 31, the prediction model storage unit 32, and the prediction result storage unit 33.

<An Operation>

Next, an operation of the emergency medical service demand prediction device 1 configured as described will be explained.

For example, the emergency medical service demand prediction device 1 is capable of starting a learning process or a predicting process, upon receipt of an instruction signal from an operator or the like that is input via an input device (not shown).

(1) An Illness/Injury Group Learning Process

Upon receipt of an instruction signal for an illness/injury group learning process, the emergency medical service demand prediction device 1 performs a process of learning the categorization model of the illness/injury groups, as described below.

Figure 2:
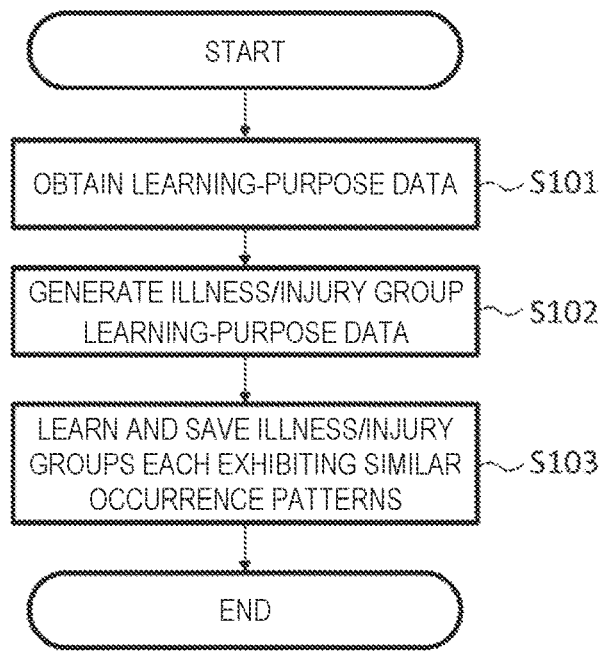
FIG. 2 is a flowchart showing an example of a categorization model learning procedure performed by the emergency medical service demand prediction device shown in FIG. 1.

FIG. 2 is a flowchart showing a processing procedure and a processing description of the process of learning the illness/injury groups performed by the emergency medical service demand prediction device 1 shown in FIG. 1.

First, at step S101, under the control of the transport data obtainment unit 21, the emergency medical service demand prediction device 1 obtains the transport data from the external emergency medical service database EMDB via the input/output interface unit 10 and further forwards the obtained transport data to the transport data pre-processing unit 22. At this time, the emergency medical service demand prediction device 1 may save the obtained transport data into the storage unit 30.

FIG. 5 shows an example of the obtained transport data. The transport data shown in FIG. 5 includes ID numbers identifying records and information indicating dates and times of occurrences, dispatch regions, age groups, genders, places of the occurrences, types of illnesses and injuries, body parts of the illnesses and injuries, degrees of the illnesses and injuries, and the like.

Subsequently, at step S102, under the control of the transport data pre-processing unit 22, the emergency medical service demand prediction device 1 generates illness/injury group learning-purpose data by performing processes such as supplementing missing information and normalization on the transport data received from the transport data obtainment unit 21 and further forwards the generated data to the illness/injury group learning unit 23.

It is considered that the number of occurrences of illnesses and injuries is impacted by a plurality of factors. Examples thereof include illnesses and injuries that disproportionately occur in a specific age group or gender. (For example, although many illnesses are often suffered by elderly people, febrile convulsion and the like often experienced by young people.) Other examples include illnesses and injuries impacted by temperature, atmospheric pressure, weather, and the like. Also, there are other examples where illnesses and injuries have regional characteristics (acute alcoholism in commercial districts, injuries and fractures in sports facilities, and illnesses and injuries in regions having frequent traffic accidents). It is possible to utilize the transport data more efficiently and more effectively, by learning those mechanisms from the data and organizing illness/injury groups that each exhibit similar occurrence patterns in various situations. In the example of the transport data shown in FIG. 5, it is possible to use, as the illness/injury group learning-purpose data, attribute information of the patients such as the age groups and the genders, as well as information about the places of occurrences of the illnesses and injuries, and the dates and times of occurrences of the illnesses and injuries, for example.

Subsequently, at step S103, under the control of the illness/injury group learning unit 23, the emergency medical service demand prediction device 1 learns the illness/injury groups that each exhibit similar occurrence patterns, by using the illness/injury group learning-purpose data and further saves the learning result to the categorization model storage unit 31 as a trained model.

For example, the illness/injury group learning unit 23 is capable of calculating degrees of similarity or distances between the illnesses and injuries and extracting the illness/injury groups on the basis of the calculated values.

FIG. 6A shows, as an example of the learning process, a result of extracting the illness/injury groups by using a K-means clustering scheme. In the example in FIG. 6A, the illnesses and injuries are divided into tens of clusters, by applying a K-means while using each of the pieces of emergency medical transport data in FIG. 5 as a node and using the patient attributes, the places of occurrences, and the dates and times of occurrences as the values of the nodes. These clusters correspond to situations in which illnesses and injuries easily occur. After that, the illnesses and injuries were grouped by performing a clustering process again while using the illnesses and injuries as nodes, and the number of occurrences of illnesses and injuries in each of the clusters as the values thereof.

Figure 6B:
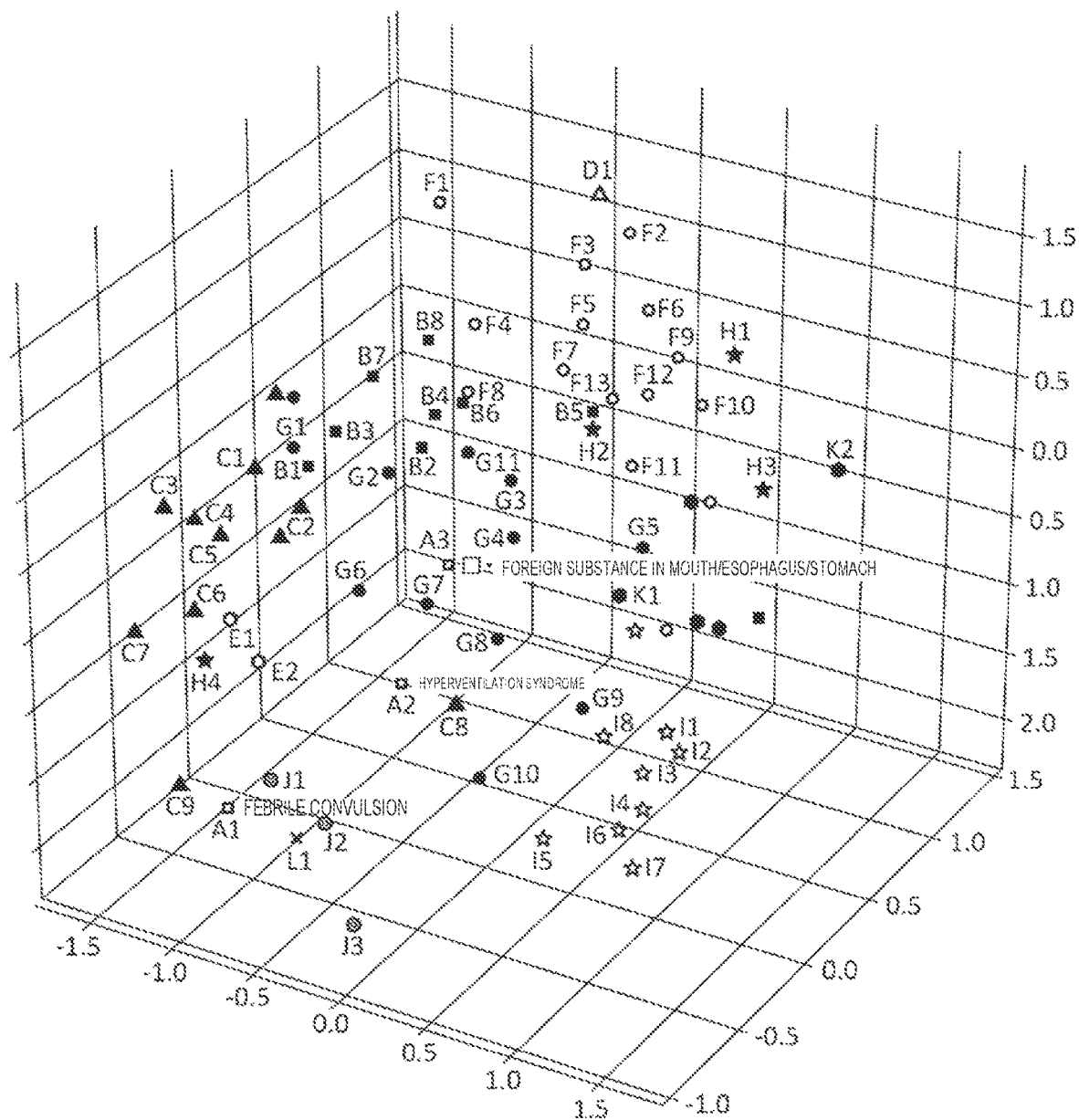
FIG. 6B is a chart showing an example of visualizing the result of extracting the illness/injury groups by using the clustering scheme.

FIG. 6B is a chart further plotting the results of the clustering process in a three-dimensional space by using a multi-dimensional scaling method for visualization. The colors and the shapes of the markers express the illness/injury groups to which the illnesses and injuries belongs. FIG. 6C indicates explanations of the markers in FIG. 6B.

From FIG. 6B, it is understood, in the present example, that symptoms that are often seen in children and young people such as febrile convulsion and hyperventilation syndrome are organized in the same illness/injury group (white square markers A1 to A3) as symptoms of having a foreign substance in the mouth, esophagus, or stomach that are probably caused by accidental ingestions. The illness/injury clustering results shown in FIGS. 6B and 6C are merely examples and are not meant to limit the scope of the embodiments.

The illness/injury group learning unit 23 is capable of saving the illness/injury groups extracted in this manner into the categorization model storage unit 31 in the form of, for example, a correspondence table between the illnesses and injuries and the illness/injury groups.

Further, the categorization model that has been trained (hereinafter, "trained categorization model") may be configured so as to perform a re-learning process while using newly-generated learning-purpose data, once every prescribed time period, when a prescribed condition is satisfied, or according to an instruction from the operator or the like.

(2) A Prediction Model Learning Process

The emergency medical service demand prediction device 1 performs a prediction model learning process as described below, upon receipt of an instruction signal to learn the prediction model from the operator, for example, following the illness/injury group learning process or separately from the illness/injury group learning process.

Figure 3:
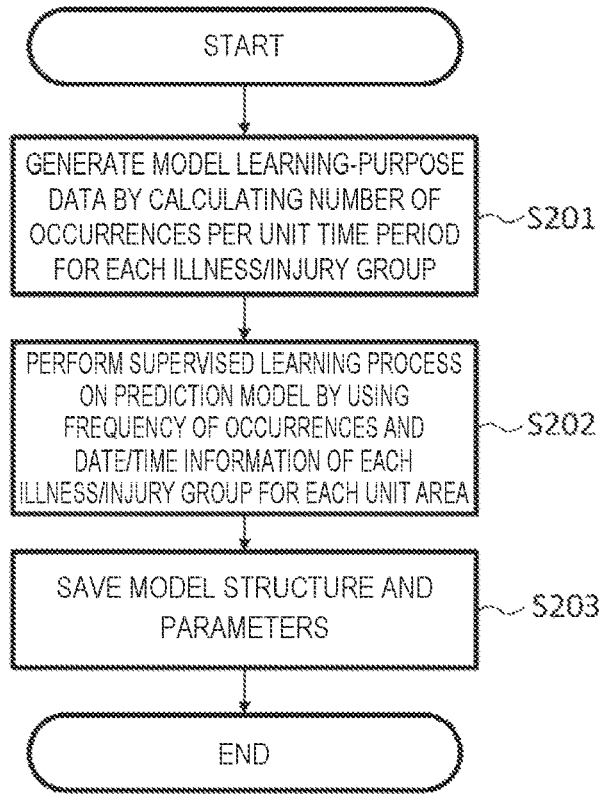
FIG. 3 is a flowchart showing an example of a prediction model learning procedure performed by the emergency medical service demand prediction device shown in FIG. 1.

FIG. 3 is a flowchart showing a processing procedure and a processing description of the process of learning the prediction model for predicting the number of occurrences of emergency medical service requests, performed by the emergency medical service demand prediction device 1 shown in FIG. 1.

First, at step S201, on the basis of the transport data obtained by the transport data obtainment unit 21, the emergency medical service demand prediction device 1 reads the trained categorization model and obtains the number of occurrences per unit time period for each illness/injury group, under the control of the transport data pre-processing unit 22. Accordingly, under the control of the transport data pre-processing unit 22, the emergency medical service demand prediction device 1 generates prediction model learning-purpose data and further forwards the generated data to the prediction model learning unit 24.

For example, at first, the transport data pre-processing unit 22 divides the transport data obtained by the transport data obtainment unit 21 into sections corresponding to unit areas, on the basis of the dispatch region information. In this situation, the unit areas may be municipal districts such as cities, wards, towns, villages, and 'chome' levels or may be region meshes calculated on the basis of latitudes and longitudes. It is possible to use an online service such as Google Maps API, for example, for conversions between the municipal districts and the latitudes and longitudes. Subsequently, on the basis of the transport data divided into the sections corresponding to the unit areas, the transport data pre-processing unit 22 performs a process of reading the trained categorization model stored in the categorization model storage unit 31 and further counting, for each unit time period, the number of occurrences of each of the illness/injury groups that have been learned.

FIG. 7 shows an example of the prediction model learning-purpose data generated in the manner described above. The example in FIG. 7 shows, with respect to "1 Chome, ** Town" serving as a unit area, the number of occurrences of emergency medical service requests for each illness/injury group that is counted for each of the time spans, as well as total numbers of occurrences obtained by adding up the occurrence values.

Subsequently, at step S202, under the control of the prediction model learning unit 24, the emergency medical service demand prediction device 1 performs a supervised learning process on the prediction model by using, as the prediction model learning-purpose data, the frequency of occurrences and the date/time information for each unit area and each illness/injury group as shown in FIG. 7. For the learning process, for example, a statistical method using a generalized linear model or a machine learning method using a random forest or a neural network may be used.

Subsequently, at step S203, under the control of the prediction model learning unit 24, the emergency medical service demand prediction device 1 is able to save the trained prediction model, i.e., an optimal model structure and parameters that have been obtained, into the prediction model storage unit 32.

The trained prediction model may be configured so as to perform a re-learning process while using newly-generated learning-purpose data, once every prescribed time period, when a prescribed condition is satisfied, or according to an instruction from the operator or the like.

(3) A Predicting Process

Upon receipt of an instruction signal for the predicting process, the emergency medical service demand prediction device 1 performs a process of predicting the number of occurrences of emergency medical service requests as described below, by using the trained categorization and prediction models.

Figure 4:
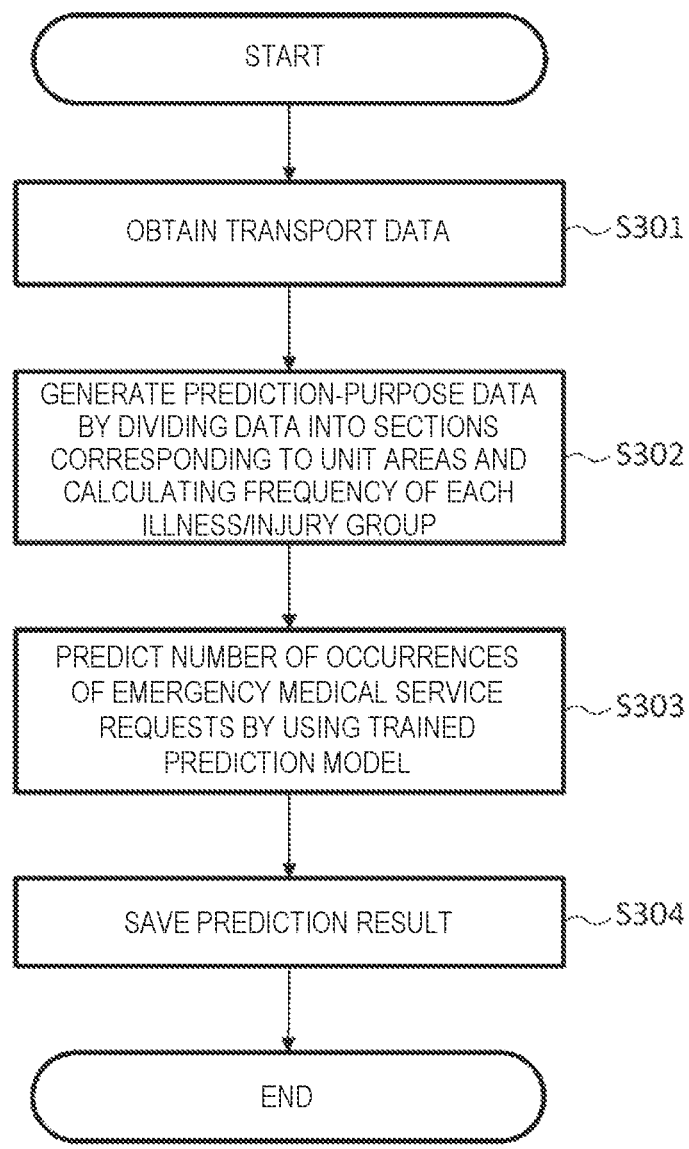
FIG. 4 is a flowchart showing an example of a predicting procedure performed by the emergency medical service demand prediction device shown in FIG. 1.

FIG. 4 is a flowchart showing a processing procedure and a processing description of the process of predicting the number of occurrences of emergency medical service requests performed by the emergency medical service demand prediction device 1 shown in FIG. 1.

First, at step S301, under the control of the transport data obtainment unit 21, the emergency medical service demand prediction device 1 obtains the transport data from the external emergency medical service database EMDB via the input/output interface unit 10 and further forwards the obtained transport data to the transport data pre-processing unit 22.

In this situation, generally speaking, there is a time lag before emergency medical transport data is collected in a database. For this reason, when the predicting process is performed in actuality, the emergency medical service demand prediction device 1 may be configured so as to obtain the transport data up to a number of hours prior from the emergency medical service database EMDB and to directly collect the most recent transport data from ambulances and the like.

Subsequently, at step S302, under the control of the transport data pre-processing unit 22, the emergency medical service demand prediction device 1 generates prediction-purpose data by performing various types of pre-processing processes on the transport data received from the transport data obtainment unit 21 and further forwards the generated prediction-purpose data to the request occurrence number prediction unit 25. For example, when the most recent transport data is directly obtained from ambulances and the like as described above, the transport data pre-processing unit 22 puts together the transport data obtained from the emergency medical service database EMDB with the most recent transport data, so as to divide the integrated data into the sections corresponding to the unit areas. After that, on the basis of the divided transport data, the transport data pre-processing unit 22 generates the prediction-purpose data to be input to the prediction model, by reading the trained categorization model stored in the categorization model storage unit 31 and further calculating the number of occurrences per unit time period for each illness/injury group.

Subsequently, at step S303, under the control of the request occurrence number prediction unit 25, the emergency medical service demand prediction device 1 predicts the number of occurrences of emergency medical service requests at an arbitrary time for each unit area (e.g., for each mesh), by reading the trained prediction model stored in the prediction model storage unit 32 on the basis of the received prediction-purpose data.

At step S304, under the control of the request occurrence number prediction unit 25, the emergency medical service demand prediction device 1 saves the prediction result into the prediction result storage unit 33.

FIG. 8 shows an example of the prediction result obtained in the manner described above. A predicted number of occurrences of emergency medical service requests is indicated for each unit area, the prediction being made for each of the time spans.

The output control unit 26 is capable of reading, at an appropriate time, the prediction result stored in the prediction result storage unit 33, generating output data on the basis of the read prediction result, and outputting the generated output data to a display device or an external device. Alternatively, the request occurrence number prediction unit 25 may be configured to directly forward the prediction result to the output control unit 26. Further, the output control unit 26 is also capable of generating the output data on the basis of the correspondence table stored in the categorization model storage unit 31 or the parameters stored in the prediction model storage unit 32, according to instructions from the operator or the like.

Regarding the learning and predicting processes described above, in an example, the emergency medical service demand prediction device 1 may be configured to perform a supervised learning process to learn a model that predicts a sum of the total numbers of occurrences at times $t_n$ to $t_{n+\alpha}$, by using the information described below. In this situation, the used information may be "p" sets of information such as the month of occurrence, the days of the week, and holidays, information related to dates and times such as time spans, and the number of occurrences of emergency medical service requests for each type of illnesses and injuries, the p sets corresponding to times $t_{n-m}$ to $t_{n-m+p}$. For example, when the number of occurrences in the next three hours is to be predicted by using the data from the last 24 hours, a problem is solved in which a sum of the total numbers of occurrences from times $t_n$ to $t_{n+2}$ is predicted by using learning-purpose data from times $t_{n-24}$ to $t_{n-1}$.

In one embodiment, the model learning process may be performed in advance by using the accumulated data, so that only the predicting process is performed during the system operation. Further, an arrangement may be made so that the model re-learning process is performed with prescribed timing (e.g., every week or every month) or when the prediction result has been found significantly incorrect for a prescribed time period.

In one example, the emergency medical service demand prediction device 1 may be configured so that the transport data pre-processing unit 22 inputs actual counted values to the table in the prediction result storage unit shown in FIG. 8 at the stage when the result is confirmed, so that a sum of errors in all the unit areas per unit time period is calculated in order to monitor the sum of errors. Further, when the sum of errors continues to exceed a threshold value, an alarm may be issued to prompt a system operator to run the re-learning process. With this operation method, it is possible to follow changes in the external environment, while keeping costs of the re-learning process down.

Second Embodiment Example

In a second embodiment example, the emergency medical service demand prediction device 1 according to an embodiment of the present invention is further configured to use environment data indicating information about environments of the places of occurrences of the emergency medical service requests, for the learning and predicting processes.

Figure 9:
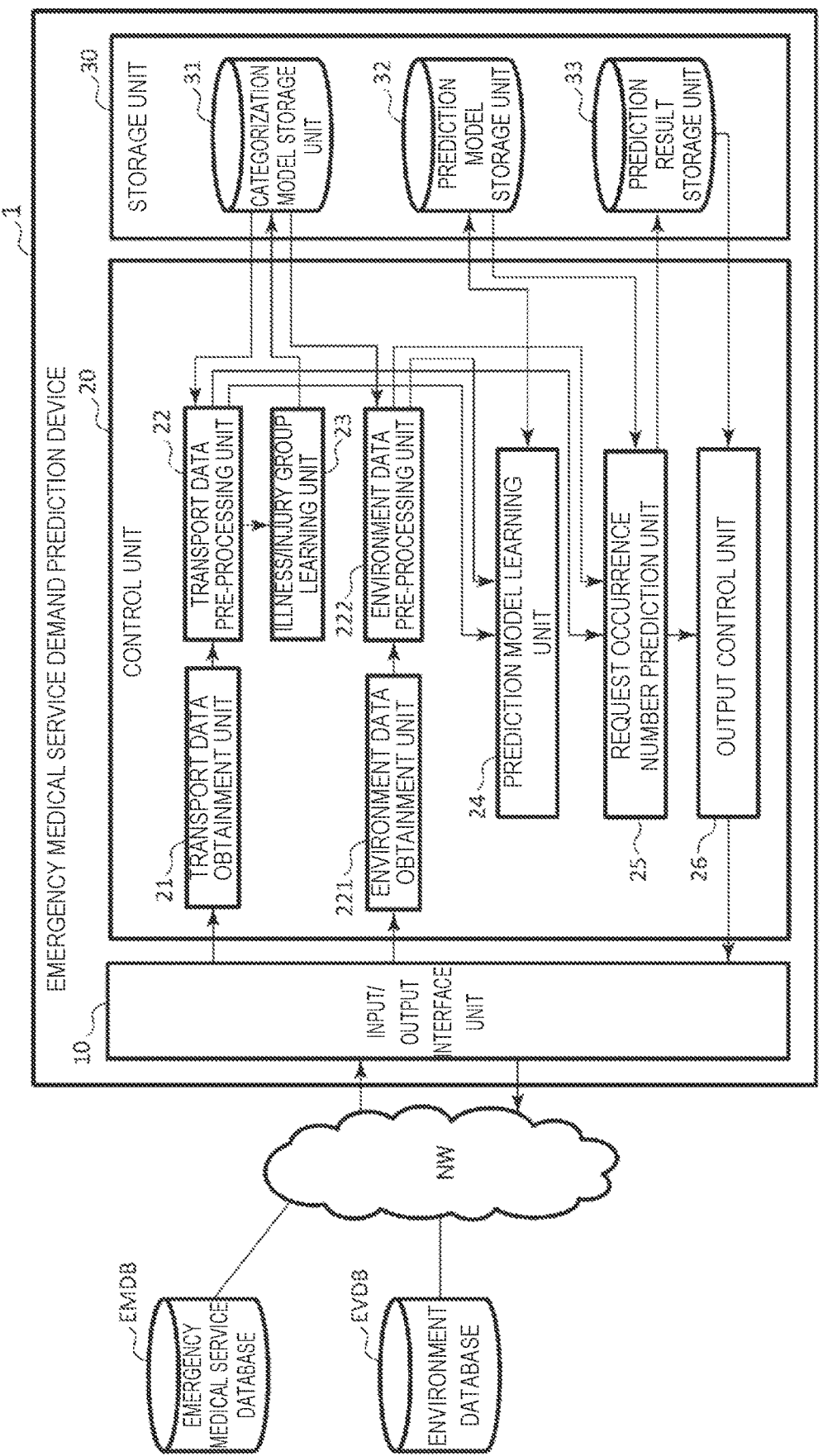
FIG. 9 is a block diagram showing a second example of the functional configuration of the emergency medical service demand prediction device according to an embodiment of the present invention.

FIG. 9 is a block diagram showing a functional configuration of the emergency medical service demand prediction device 1 according to the second embodiment example. In FIG. 9, some of the constituent elements that are the same as those in FIG. 1 are referred to by using the same reference characters, and detail explanations thereof will be omitted.

In comparison to the device shown in FIG. 1, the emergency medical service demand prediction device 1 in FIG. 9 further includes, within the control unit 20, an environment data obtainment unit 221 and an environment data pre-processing unit 222. Further, in addition to with the emergency medical service database EMDB, the emergency medical service demand prediction device 1 in FIG. 9 is also capable of communicating with an environment database EVDB via the network NW.

For example, upon receipt of an instruction signal for the learning process or the predicting process input by the operator, the environment data obtainment unit 221 performs a process of obtaining environment data such as meteorological data from the environment database EVDB via the input/output interface unit 10 and further forwarding the obtained data to the environment data pre-processing unit 222. The environment database EVDB is, for example, connected to an environment data collection server that collects information related to the surrounding environment, from the Internet or an external service, either automatically or through manual operations of the operator. The environment database EVDB has accumulated therein the collected environment data.

FIG. 10 shows an example of the obtained environment data. An example of the environment data is meteorological data obtained from the homepage of the Japan Meteorological Agency. In FIG. 10, various types of meteorological data are displayed together with the date/time information. Also, information indicating the situations in which the pieces of data were obtained are appended as Conditions 1, 2, and 3. In one example, Condition 1 indicates whether there is any missing data in the data on which the statistics are based. Condition 2 indicates differences in the observation environments. Condition 3 is information indicating whether the corresponding event occurred or not by using the values 0 and 1.

On the environment data received from the environment data obtainment unit 221, the environment data pre-processing unit 222 performs pre-processing processes such as extracting necessary items, supplementing missing information, and performing normalization. FIG. 11 shows an example of the environment data on which the pre-processing processes have been performed. The environment data pre-processing unit 222 forwards the pre-processed environment data to one of the prediction model learning unit 24 and the request occurrence number prediction unit 25.

The prediction model learning unit 24 and the request occurrence number prediction unit 25 are capable of performing the learning and predicting processes, by matching the learning-purpose or prediction-purpose data received from the transport data pre-processing unit 22 with the environment data received from the environment data obtainment unit 221, on the basis of time information.

Third Embodiment Example

In a third embodiment example, the emergency medical service demand prediction device 1 according to an embodiment of the present invention is further configured to use region data including regional statistic information of the places of occurrences of the emergency medical service requests, for the learning and predicting processes.

Figure 12:
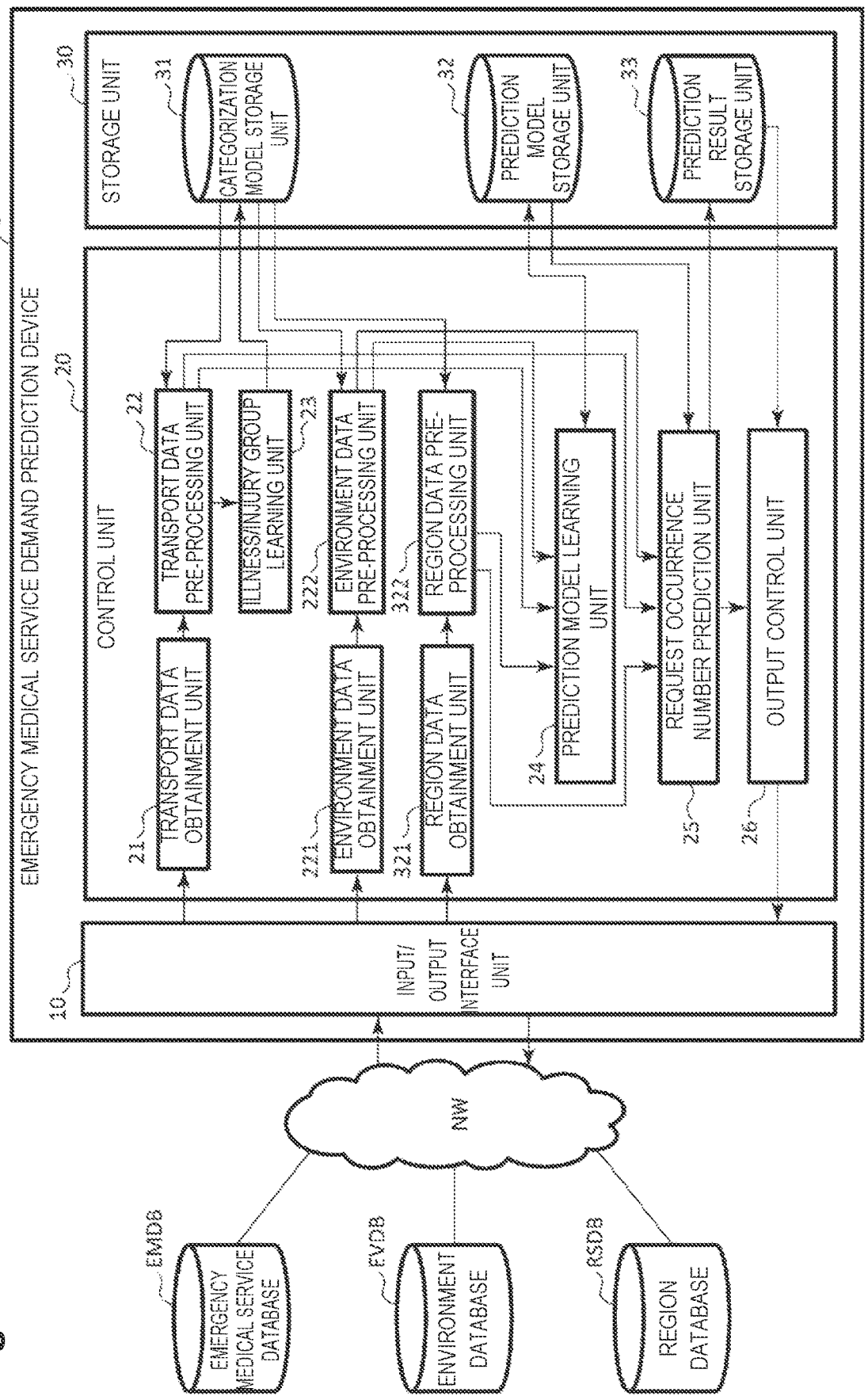
FIG. 12 is a block diagram showing a third example of the functional configuration of the emergency medical service demand prediction device according to an embodiment of the present invention.

FIG. 12 is a block diagram showing a functional configuration of the emergency medical service demand prediction device 1 according to the third embodiment example. In FIG. 12, some of the constituent elements that are the same as those in FIG. 1 or FIG. 9 are referred to by using the same reference characters, and detail explanations thereof will be omitted.

In comparison to the device shown in FIG. 9, the emergency medical service demand prediction device 1 in FIG. 12 further includes, within the control unit 20, a region data obtainment unit 321 and a region data pre-processing unit 322. Further, in addition to with the emergency medical service database EMDB and the environment database EVDB, the emergency medical service demand prediction device 1 in FIG. 12 is also capable of communicating with a region database RSDB via the network NW.

For example, upon receipt of an instruction signal for the learning or predicting process input by the operator, the region data obtainment unit 321 performs a process of obtaining region data from the region database RSDB via the input/output interface unit 10 and further forwarding the obtained data to the region data pre-processing unit 322. The region database RSDB is, for example, connected to a region data collection server that collects information related to the regional statistics, from the Internet or an external service, either automatically or through manual operations of the operator. The region database RSDB has accumulated therein the collected region data. Examples of the regional statistic information contained in the region data include: map information storing facility information of hospitals, shops, and the like in the regions; and information about populations in age groups for each of the unit areas.

On the region data received from the region data obtainment unit 321, the region data pre-processing unit 322 performs region data re-shaping processes such as aggregating data for each unit area, adjusting intervals, and supplementing missing information. The region data pre-processing unit 322 forwards the pre-processed region data to one of the prediction model learning unit 24 and the request occurrence number prediction unit 25.

FIG. 13 shows, as an example of the region data, population transition data for different genders and age groups. It is possible to generate the data by, for example, bringing subscriber information into association with terminal device information collected by base stations of mobile phones.

In population distribution data corresponding to different times, the number of people smaller than a threshold value may be masked and shown as blank for the purpose of protecting privacy. In that situation, the region data pre-processing unit 322 is capable of supplementing the missing information in the data, for example, by using a monthly average population recorded as an estimated population or an official registration population prepared by each municipality so as to calculate a value that makes a regional sum of nighttime populations equal to the monthly average population.

The prediction model learning unit 24 and the request occurrence number prediction unit 25 are capable of performing the learning and predicting processes by matching the following three types of data with one another, on the basis of time information. The first type of data is the learning-purpose or prediction-purpose data received from the transport data pre-processing unit 22. The second type of data is the environment data received from the environment data obtainment unit 221. The third type of data is the region data received from the region data obtainment unit 321.

Alternatively, it is also acceptable to omit the environment data obtainment unit 221 and the environment data pre-processing unit 222 from the emergency medical service demand prediction device 1 according to the third embodiment example, so as not to use the environment data in the learning and predicting processes.

Fourth Embodiment Example

In a fourth embodiment example, the emergency medical service demand prediction device 1 according to an embodiment of the present invention is further configured to learn regional characteristics of each unit area on the basis of the region data indicating the regional statistic information of the places of occurrences of the emergency medical service requests and to use a learning result for the learning and predicting processes described above.

Figure 14:
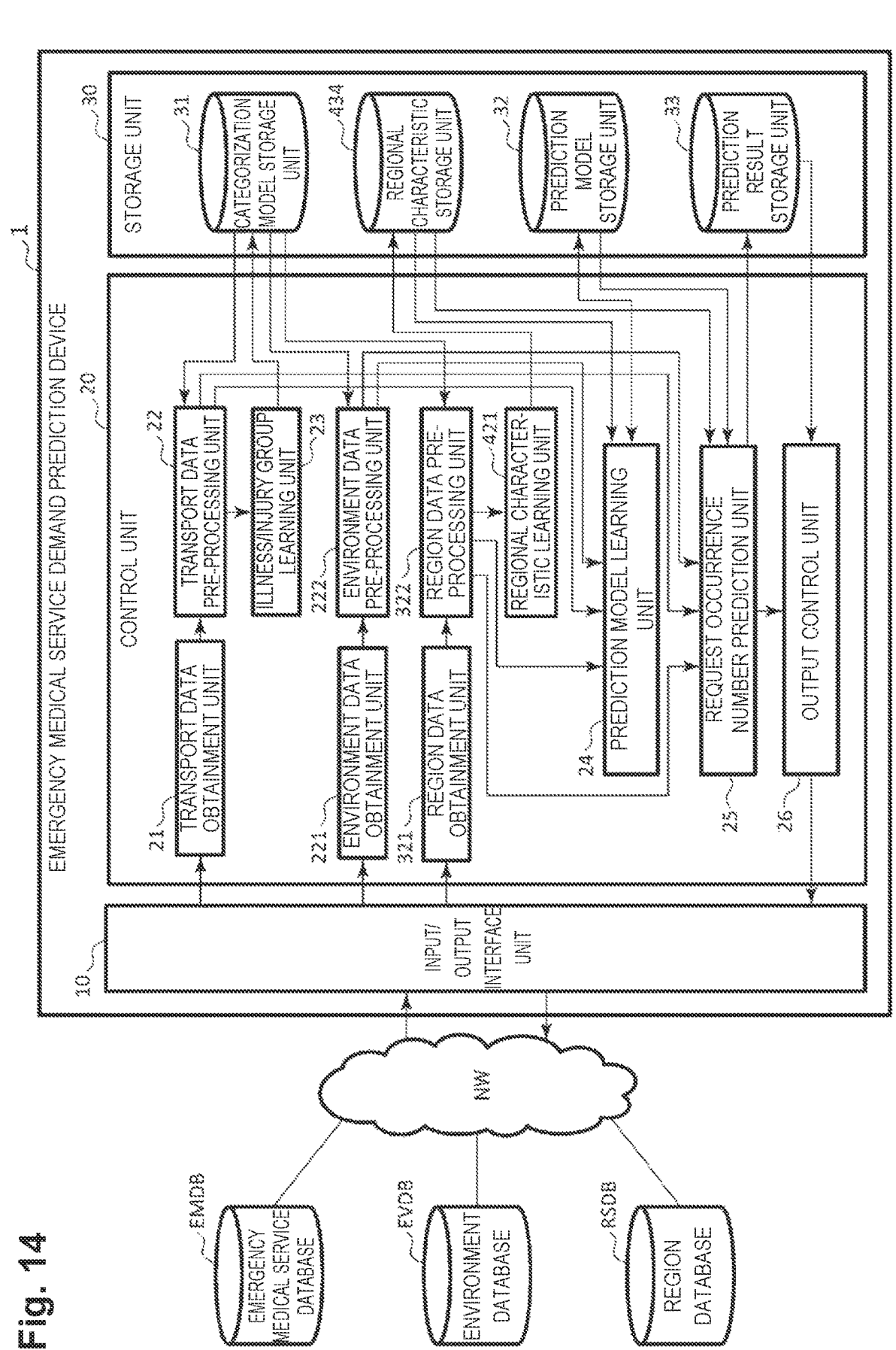
FIG. 14 is a block diagram showing a fourth example of the functional configuration of the emergency medical service demand prediction device according to an embodiment of the present invention.

FIG. 14 is a block diagram showing a functional configuration of the emergency medical service demand prediction device 1 according to the fourth embodiment example. In FIG. 14, some of the constituent elements that are the same as those in FIG. 1, 9, or 12 are referred to by using the same reference characters, and detail explanations thereof will be omitted.

In comparison to the device shown in FIG. 12, the emergency medical service demand prediction device 1 in FIG. 14 further includes a regional characteristic learning unit 421 within the control unit 20 and includes a regional characteristic storage unit 434 within the storage unit 30.

Similarly to the third embodiment example, the emergency medical service demand prediction device 1 shown in FIG. 14 obtains the region data under the control of the region data obtainment unit 321 and performs a prescribed pre-processing process on the obtained region data under the control of the region data pre-processing unit 322. The region data pre-processing unit 322 forwards the pre-processed region data to one of the prediction model learning unit 24, the request occurrence number prediction unit 25, and the regional characteristic learning unit 421. For example, on the basis of the obtained region data, the region data pre-processing unit 322 is capable of performing one of the following: generating learning-purpose region data to forward the generated data to the prediction model learning unit 24; generating prediction-purpose region data to forward the generated data to the request occurrence number prediction unit 25; and generating regional characteristic learning-purpose data to forward the generated data to the regional characteristic learning unit 421.

The regional characteristic learning unit 421 functions as the third learning unit and, while using the received regional characteristic learning-purpose data, performs a process of learning and extracting information indicating what type of district the region is, on the basis of the population data for each time span and each age group, as well as the numbers of hospitals, nursing homes, shops, schools, sports facilities, and the like in the areas.

FIG. 15 shows an example of the regional characteristic learning-purpose data. It is possible to obtain the types and the numbers of facilities in the areas, by conducting searches in various types of map services such as Google Maps API.

The regional characteristic learning unit 421 does not function when the learning process is performed on a single unit area, but becomes able to extract an emergency medical service request occurrence pattern corresponding to the nature of districts such as business districts and commercial districts or the nature of residents such as a mature residential area or a newly-developed residential area, by performing a learning process on various types of unit areas and having the parameters thereof handed over.

The regional characteristic storage unit 434 stores therein the learning result obtained by the regional characteristic learning unit 421. Similarly to the storage units 31, 32, and 33, the regional characteristic storage unit 434 is not a requisite configuration and may be replaced by an external storage medium or the like.

FIG. 16 shows, as an example of the learning result obtained by the regional characteristic learning unit 421, a result of conjecturing whether each of the areas may have the nature of a business district, a commercial district, a residential area, or the like, on the basis of population fluctuations and the facilities that are present in the area.

The prediction model learning unit 24 and the request occurrence number prediction unit 25 are capable of performing the learning and predicting processes described above, on the basis of the region data pre-processed by the region data pre-processing unit 322 and feature values expressing the regional characteristics and having been extracted by the regional characteristic learning unit 421.

Alternatively, it is also acceptable to omit the environment data obtainment unit 221 and the environment data pre-processing unit 222 from the emergency medical service demand prediction device 1 according to the fourth embodiment example, so as not to use the environment data in the learning and predicting processes.

Fifth Embodiment Example

The emergency medical service demand prediction device 1 in the first embodiment example independently extracts the illness/injury groups by using the clustering scheme; however, the illness/injury group extracting process and the prediction model learning process may be performed simultaneously.

In a fifth embodiment example, the emergency medical service demand prediction device 1 according to an embodiment of the present invention is configured to simultaneously perform the illness/injury group extracting process and the prediction model learning process, by adding a layer corresponding to the illness/injury group learning process to the model in a neural network, for example.

In the fifth embodiment example, for instance, a Long Short-term Memory [LSTM] (a type of recurrent neural network) layer is prepared for the illness/injury group extracting process and for the occurrence number predicting process. To the LSTM layer for the illness/injury group extracting process, it is possible to input a count of the number of occurrences of emergency medical service requests per unit time period, for each of various types of illnesses and injuries determined by each municipality. Further, by setting the number of output nodes to a small value (approximately 20 to 30) relative to the original number of illness/injury categories, it is possible to achieve an advantageous effect where the illness/injury categories are summarized. By setting the output as an input to the LSTM layer for the emergency medical service request occurrence number predicting process and proceeding with the learning process collectively, it is possible to extract illness/injury groups that improve the level of precision of the occurrence number prediction to a maximum extent.

(1) The Learning Process

Figure 17:
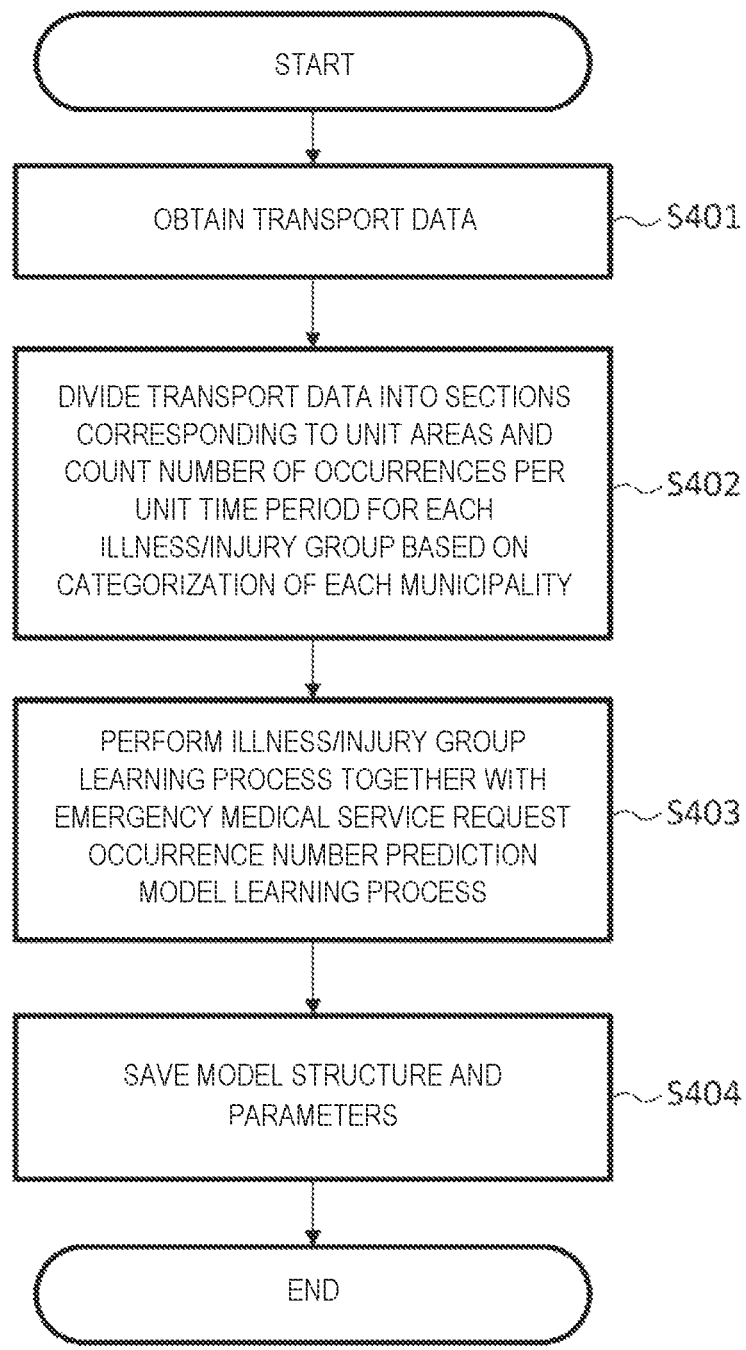
FIG. 17 is a flowchart showing a second example of a learning procedure performed by the emergency medical service demand prediction device according to an embodiment of the present invention.

FIG. 17 is a flowchart showing the processes of learning the illness/injury groups and the prediction model performed by the emergency medical service demand prediction device 1 according to the fifth embodiment example. The basic configuration of the emergency medical service demand prediction device 1 according to the fifth embodiment example is the same as that of the emergency medical service demand prediction device 1 shown in FIG. 1, except how the functions are executed is different. Thus, in the following sections, processes will be explained by using the reference characters of the constituent elements of the emergency medical service demand prediction device 1 shown in FIG. 1.

First, at step S401, under the control of the transport data obtainment unit 21, the emergency medical service demand prediction device 1 obtains the transport data from the external emergency medical service database EMDB via the input/output interface unit 10 and further forwards the obtained transport data to the transport data pre-processing unit 22.

Subsequently, at step S402, under the control of the transport data pre-processing unit 22, the emergency medical service demand prediction device 1 divides the transport data received from the transport data obtainment unit 21 into sections corresponding to the unit areas and further generates model learning-purpose data by counting the number of occurrences per unit time period for each of the illnesses and injuries based on the categorization of each municipality.

FIG. 19 shows an example of the model learning-purpose data. To the LSTM layer for the illness/injury group extracting process, it is possible to input the count of the number of occurrences of emergency medical service requests per unit time period, for each of the various types of illnesses and injuries determined by each municipality, as shown in FIG. 19.

Subsequently, at step S403, the emergency medical service demand prediction device 1 performs the illness/injury group learning process by the illness/injury group learning unit 23, together with the prediction model learning process by the prediction model learning unit 24.

At step S404, the emergency medical service demand prediction device 1 saves a model structure and parameters related to the trained prediction model into the prediction model storage unit 32, for example.

(2) A Predicting Process

Figure 18:
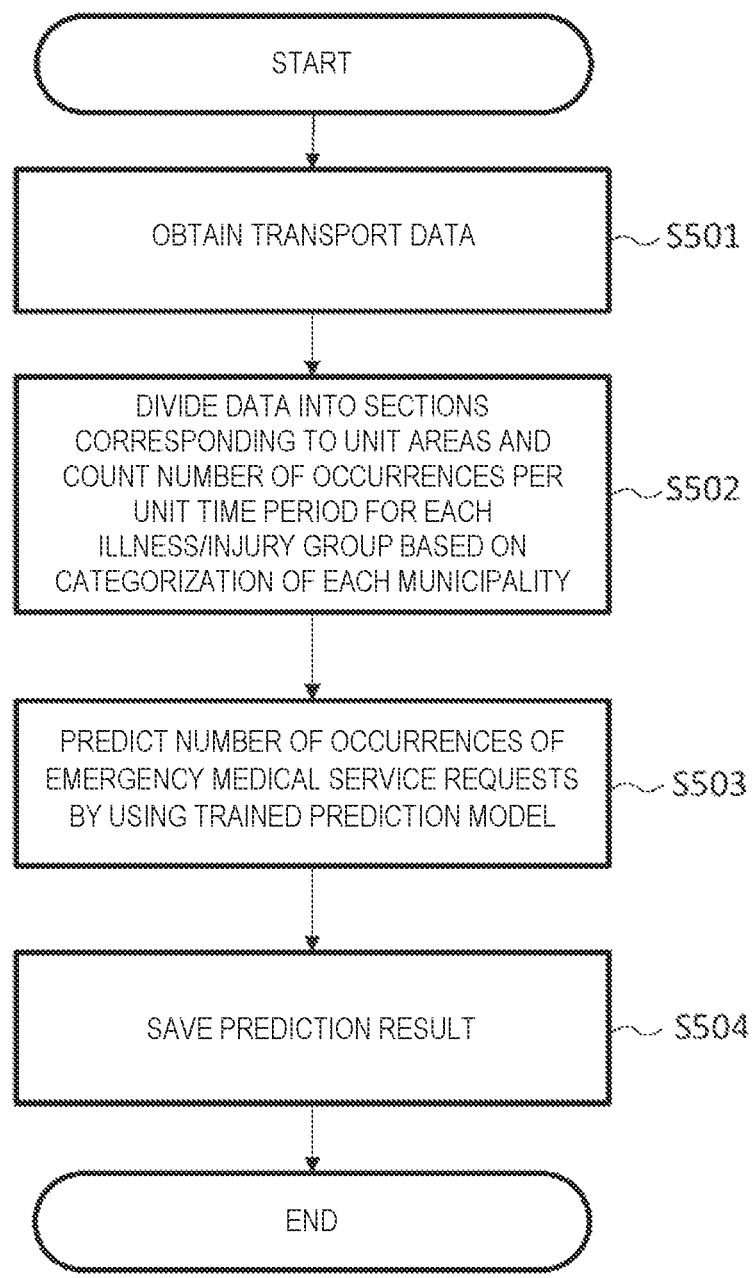
FIG. 18 is a flowchart showing a second example of the predicting procedure performed by the emergency medical service demand prediction device according to an embodiment of the present invention.

FIG. 18 is a flowchart showing the predicting process performed by the emergency medical service demand prediction device 1 according to the fifth embodiment example. Again, processes will be explained by using the reference characters of the constituent elements of the emergency medical service demand prediction device 1 shown in FIG. 1.

First, at step S501, under the control of the transport data obtainment unit 21, the emergency medical service demand prediction device 1 obtains the transport data from the external emergency medical service database EMDB via the input/output interface unit 10 and further forwards the obtained transport data to the transport data pre-processing unit 22. As explained in the first embodiment example, in the actual predicting process, the emergency medical service demand prediction device 1 may directly collect the most recent transport data from ambulances and the like, in consideration of the time lag before certain emergency medical transport data is collected into the database.

Subsequently, at step S502, under the control of the transport data pre-processing unit 22, the emergency medical service demand prediction device 1 divides the transport data received from the transport data obtainment unit 21 into sections corresponding to the unit areas and further generates prediction-purpose data by counting the number of occurrences per unit time period for each of the illnesses and injuries based on the categorization of each municipality.

At step S503, under the control of the request occurrence number prediction unit 25, while using the trained prediction model that has been learned as described above, the emergency medical service demand prediction device 1 predicts the number of occurrences of emergency medical service requests for each unit area on the basis of the prediction-purpose data.

At step S504, under the control of the control unit 20, the emergency medical service demand prediction device 1 saves the prediction result obtained by the request occurrence number prediction unit 25, into the prediction result storage unit 33.

Further, similarly to the illness/injury group extracting process, the regional characteristic learning process described in the fourth embodiment example may also be performed simultaneously together with the prediction model learning process. In that situation, for example, by incorporating the regional characteristic extracting process and the emergency medical service request occurrence number predicting process into mutually the same model by using a neural network, it is possible to optimize both at the same time. More specifically, for example, the regional characteristic learning unit 421 may be configured as an LSTM layer that receives an input of a distribution of population for each age group corresponding to the days of the week and time spans and the facility information in the areas and outputs approximately 10 to 20 nodes corresponding to different types of districts.

Figure 20:
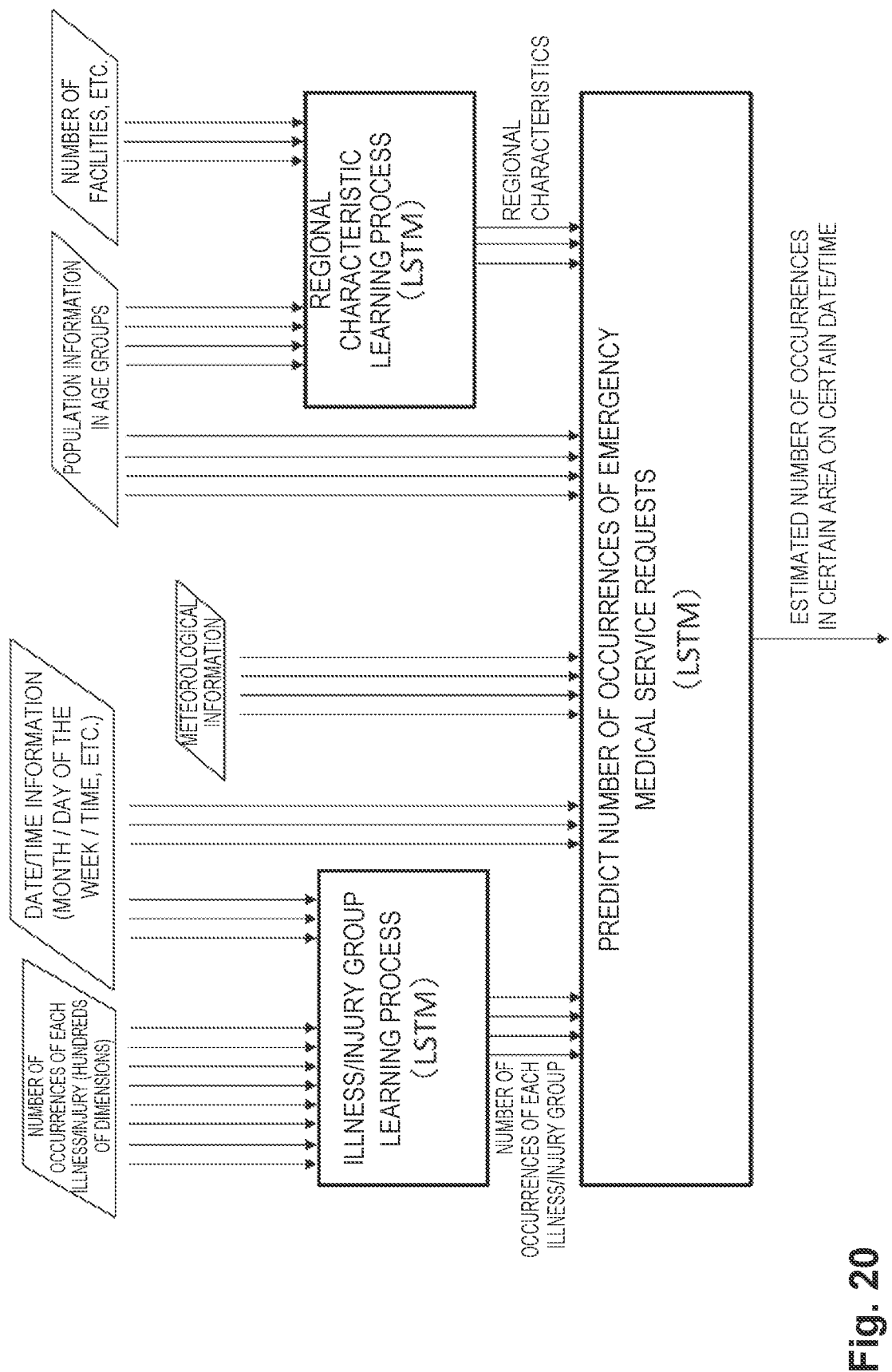
FIG. 20 is a schematic chart showing data flows in the learning procedure in FIG. 17 and the predicting procedure in FIG. 18.

FIG. 20 shows an outline of data flows in the learning model using the LSTM layer according to the fifth embodiment example described above. The emergency medical service demand prediction device 1 shown in FIG. 20 uses an LSTM layer that receives an input of the data indicating the number of occurrences for each type of illnesses and injuries obtained from each municipality for extracting the illness/injury groups and further uses the output of the LSTM layer as an input to a prediction-purpose LSTM. Similarly, the emergency medical service demand prediction device 1 uses an LSTM layer for extracting regional characteristic feature values and further uses the output of the LSTM layer as an input to a prediction-purpose LSTM.

Sixth Embodiment Example

In a sixth embodiment example, the emergency medical service demand prediction device 1 according to an embodiment of the present invention is further configured so that the output control unit 26 serves as a prediction result output unit and generates and outputs output data for visually displaying the prediction result. The emergency medical service demand prediction device 1 according to the sixth embodiment example may have the same functional configuration as that of any of the emergency medical service demand prediction devices 1 described in the first to the fifth embodiment examples.

Figure 21A:
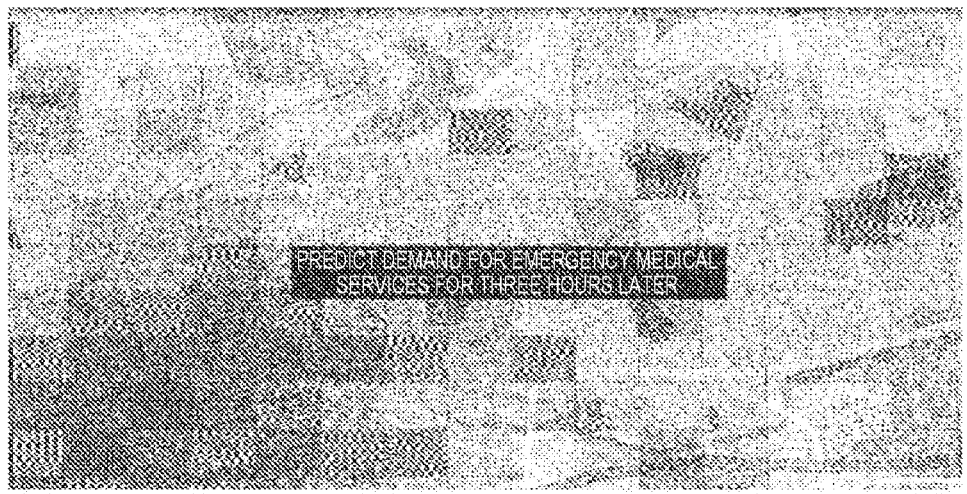
FIG. 21A is a drawing showing a first example of visually displaying results of predicting an emergency medical service demand.
Figure 21B:
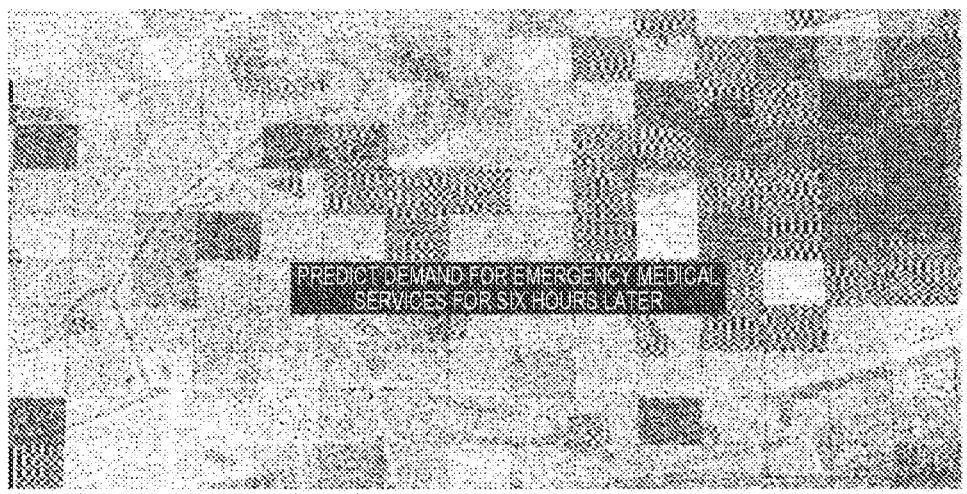
FIG. 21B is a drawing showing a second example of visually displaying results of predicting an emergency medical service demand.

FIGS. 21A and 21B show examples of the display based on the output data output from the emergency medical service demand prediction device 1 according to the sixth embodiment example in which prediction results are visualized on heat maps. These images may be displayed on a display device such as a liquid crystal display device.

FIG. 21A shows an emergency medical service demand prediction result for three hours later, predicted on the basis of the most recent data. FIG. 21B shows an emergency medical service demand prediction result for six hours later, similarly predicted on the basis of the most recent data. From FIGS. 21A and 21B, it is observed that, between the predictions for the three hours later and for the six hours later, the area predicted with a larger number of occurrences of emergency medical service requests (the darker meshes in the heat maps) has shifted from the lower left corner to the upper right corner. The emergency medical service demand prediction device 1 according to the sixth embodiment example is also capable of assisting exploring the utilization of emergency medical staff, by depicting transitions of predicted values in a specific area in a graph or a table. Further, the output format of the prediction result from the emergency medical service demand prediction device 1 according to the sixth embodiment example is not limited to visual presentation. It is possible to output the result in various formats including a synthetic voice.

Advantageous Effects

As explained in detail above, the emergency medical service demand prediction device according to the one embodiment is capable, in emergency medicine, of predicting the number of occurrences of emergency medical service requests in the near future, from the transport data including the dates and times of occurrences and the places of occurrences of the emergency medical service requests from the past. At that time, the emergency medical service demand prediction device according to the one embodiment divides the past emergency medical transport data into the pieces of data corresponding to the unit areas, so as to calculate the number of occurrences in each area for each unit time period and each type of illnesses and injuries as a feature value, and to subsequently learn the illness/injury groups that are each impacted by the same type of environment factors. Further, the emergency medical service demand prediction device according to the one embodiment performs the learning and predicting processes by using the calculated number of occurrences for each illness/injury group that has been learned, as the learning-purpose data and the prediction-purpose data.

With these arrangements, even when the obtained actual history data of the emergency medical transports do not have sufficiently high frequency of occurrences that can withstand analyses in units of illnesses and injuries, it is possible to predict the number of occurrences of the emergency medical service requests with an excellent level of precision from the limited actual history data, by learning the illness/injury groups and calculating the frequency of occurrences for each illness/injury group to be used in the analyses.

Further, as described above, illnesses and injuries are considered to be impacted by a plurality of factors, since the numbers of occurrences of certain illnesses and injuries are disproportionately high in a specific age group or gender, while certain illnesses and injuries are impacted by temperature, atmospheric pressure, or weather or exhibit regional characteristics. The emergency medical service demand prediction device according to the one embodiment learns the mechanism of these factors from the data and organizes the illness/injury groups that each exhibit the similar occurrence patterns in various situations. It is therefore possible to absorb differences in the manual categorization and to handle the data of the number of occurrences of the emergency medical service requests for each type of illnesses and injuries, with optimal granularity.

Further, generally speaking, many illnesses are impacted by temperature or weather, (e.g., a cold, the influenza, heatstroke, etc.). Further, changes in the atmospheric pressure are known to disturb the autonomic nerves and cause various illnesses such as headaches, nerve pains, and strokes. The emergency medical service demand prediction device according to the one embodiment incorporates these impacts in the models by performing the learning and predicting processes while using the environment data such as the meteorological data. It is thus expected to be possible to achieve an advantageous effect where the levels of precision of the predictions are improved.

Further, typified by the fact that newly-developed residential areas attract families raising children, residential areas often attract residents who belong to similar age groups or who have similar financial statuses, values, and/or lifestyles. Further, requests for emergency medical service dispatches strongly reflect regional characteristics in that, for example, regions having a hospital experience a certain ratio of emergency medical service dispatches for inter-hospital transports, and in commercial districts, the number of requests for an emergency medical service dispatch increases during nighttime for acute alcoholism. The emergency medical service demand prediction device according to the one embodiment is able to incorporate the impacts of these factors in the models, by performing the learning and predicting processes that utilize the regional characteristics and is thus able to improve the levels of precision of the predictions.

Further, generating and outputting the output data by using a heat map or the like so as to visualize the prediction result makes it possible to understand the prediction result easily and efficiently in the actual emergency medical situations where prompt reactions are required. Further, by using a graph or the like, it is also possible to easily visualize chronological transitions in the number of occurrences of emergency medical service requests. Consequently, it is possible to visualize an estimated number of dispatches of emergency medical staff predicted for a number of hours later and to thus improve the efficiency in utilization of the emergency medical staff.

As explained above, the emergency medical service demand prediction device according to the one embodiment is able to predict the number of occurrences of emergency medical service requests with an excellent level of precision from the limited observation data, by extracting the illness/injury groups that each have similar occurrence patterns from the past emergency medical transport data and performing the learning process on the basis of the number of occurrences of each illness/injury group. Further, the emergency medical service demand prediction device according to the one embodiment is able to estimate the number of occurrences of emergency medical service requests in each area with a high level of precision by using various types of data in combination, such as the emergency medical transport data collected from the control offices and the emergency medical staff, the meteorological data that is available online, the regional characteristics of each of the unit areas, and the distribution of population per unit time period by the age groups. Further, it is possible to absorb the differences among the municipalities in the categorizations of the illnesses and injuries in the emergency medical transport data and to thus easily construct the models that are usable across the plurality of municipalities.

Other Embodiments

Possible embodiments of the present invention are not limited to those described above. For example, the trained model and the parameters saved in the prediction model storage unit 32 may conform to parameter-saving processes and file formats compliant with a statistical analysis tool being used. Similarly, the formats of the data saved in the categorization model storage unit 31, the prediction result storage unit 33, and the regional characteristic storage unit 434 are not limited to the examples presented in the drawings. It is acceptable to use arbitrary formats.

Further, possible methods for the illness/injury group learning process and the prediction model learning process are not limited to the statistical method and the machine learning method described above. It is acceptable to use arbitrary methods.

In the above example, the environment data including the meteorological information and the region data including the facility information and the population information are used for the learning and predicting processes of the prediction model; however, it is acceptable to also use these pieces of data for the illness/injury group learning process. In particular, in the embodiment examples in which the categorization model learning process is performed separately from the prediction model learning process, it is expected that it is possible to perform the illness/injury group learning process more efficiently, by using the environment data and the region data.

Further, it is possible to combine, to replace with a similar element, or to omit any of the functional units of the emergency medical service demand prediction device 1 described in the first to the sixth embodiment examples. For example, as described earlier, it is possible to configure the third and the fourth embodiment examples so that the learning and predicting processes are performed on the basis of the transport data and the region data without using the environment data.

Alternatively, the functional units 21 to 26 included in the emergency medical service demand prediction device 1 may be provided in a cloud computer, an edge router, and the like in a distributed manner, so that the learning and predicting processes are performed as a result of these devices collaborating with one another. With this arrangement, it is possible to reduce the processing loads of the devices and to thus improve the efficiency of the processes.

In addition, it is possible to carry out the present disclosure while modifying the types of the environment data and the region data, or the like, without departing from the scope of the present invention.

That is to say, the present invention is not limited to the embodiments described above. At the stage of carrying out the present disclosure, it is possible to embody the present invention while modifying the constituent elements without departing from the scope thereof. Further, it is possible to structure various inventions by combining two or more of the constituent elements disclosed in the above embodiments, as appropriate. For example, some of the constituent elements described in any of the embodiments may be omitted. Also, it is also acceptable to combine, as appropriate, constituent elements from mutually-different embodiments.

REFERENCE SIGNS LIST

1 Emergency medical service demand prediction device
10 Input/output interface unit
20 Control unit
21 Transport data obtainment unit
22 Transport data pre-processing unit
23 Illness/injury group learning unit
24 Prediction model learning unit
25 Request occurrence number prediction unit
26 Output control unit
30 Storage unit
31 Categorization model storage unit
32 Prediction model storage unit
33 Prediction result storage unit
221 Environment data obtainment unit
222 Environment data pre-processing unit
321 Region data obtainment unit
322 Region data pre-processing unit
421 Regional characteristic learning unit
434 Regional characteristic storage unit

The invention claimed is:

1. An emergency medical service demand prediction device that predicts a quantity of occurrences of emergency medical service requests in a target area, the emergency medical service demand prediction device comprising:
a memory configured to store computer program instructions; and
a processor configured to execute the computer program instructions so as to:
obtain actual history data including transport data from an external emergency medical service database, information transmitted from ambulances currently responding to the emergency medical service requests, date/time information indicating dates and times of occurrences of the emergency medical service requests, position information indicating places of the occurrences of the emergency medical service requests, illness/injury information indicating illnesses and injuries that caused the emergency medical service requests, and attribute information of patients including ages and genders;
pre-process the actual history data by dividing the actual history data into sections, extracting related items, and performing a normalization process to generate:
illness/injury group learning-purpose data used for learning the illnesses and injuries;
prediction model learning-purpose data used for learning a prediction model based on an actual number of the occurrences, the date/time information of each of the illnesses and injuries, and the position information; and
request occurrence number prediction-purpose data used for predicting a quantity of occurrences of future emergency medical service requests;
generate a first learning model, based on the illness/injury group learning-purpose data, including illness/injury groups in which the illnesses and injuries are grouped by a type of the illnesses and injuries by learning occurrence patterns of the illnesses and injuries, and similarities or distances among the illnesses and injuries in association with the dates and times, the position information, and the attribute information of the patients;
generate a second learning model, based on the first leaning model and the prediction model learning-purpose data, including a learned prediction model in which a relationship among a number of occurrences of the illnesses and injuries, the illness/injury groups, the dates and times, and the position information are learned, the learned prediction model indicating an actual number of the occurrences of the emergency medical service requests by the illness/injury groups, unit time, and unit areas in the position information;
predict the quantity of the occurrences of the future emergency medical service requests in each of the unit areas within the target area based on the second learning model and the request occurrence number prediction-purpose data; and
output the predicted quantity of the occurrences of the future emergency medical service requests to an external device.

2. The emergency medical service demand prediction device according to claim 1,
wherein the processor is further configured to:
obtain environment data including information related to meteorology of the places of the occurrences of the emergency medical service requests;
generate the second learning model by further receiving an input of the environment data; and
predict the quantity of the occurrences of the future emergency medical service requests for each of the unit areas, by further inputting the environment data to the second learning model having been trained.

3. The emergency medical service demand prediction device according to claim 1,
wherein the processor is further configured to:
obtain region data including information related to a regional statistic of the places of the occurrences of the emergency medical service requests;
generate the second learning model by further receiving an input of the region data; and
predict the quantity of the occurrences of the future emergency medical service requests for each of the unit areas, by further inputting the region data to the second learning model having been trained.

4. The emergency medical service demand prediction device according to claim 1,
wherein the processor is further configured to:
obtain region data including information related to a regional statistic of the places of the occurrences of the emergency medical service requests;
generate a third learning model which receives an input of the region data and output a regional feature value for each of the unit areas;
generate the second learning model by further receiving an input of the regional feature value output from the third learning model; and
predict the quantity of the occurrences of the future emergency medical service requests for each of the unit areas by further inputting the regional feature value output from the third learning model having been trained, to the second learning model having been trained.

5. The emergency medical service demand prediction device according to claim 1, wherein
the first learning model is structured by using a first layer of a neural network, and the second learning model is structured by using a second layer of the neural network that receives an output of the first layer as an input.

6. The emergency medical service demand prediction device according to claim 1,
wherein the processor is configured to generate and output the predicted quantity of the occurrences of the future emergency medical service requests to the external device for visually presenting a prediction result.

7. The emergency medical service demand prediction device according to claim 1,
wherein the processor is further configured to:
determine whether the predicted quantity of the occurrences of the future emergency medical service requests deviates an actual quantity of the occurrences of the future emergency medical service requests in each of the unit areas within the target area in the future for a predetermined period of time; and
perform a re-learn process in which the obtaining of the actual history data, the pre-processing of the actual history data, the generating the first learning model, the generating the second learning model, the predicting of the quantity of the occurrences of the future emergency medical service requests, and the outputting the predicted quantity of the occurrences of the future emergency medical service requests are repeated when the processor determines that the predicted quantity of the occurrences of the future emergency medical service requests deviates the actual quantity of the occurrences of the future emergency medical service requests in each of the unit areas within the target area in the future for the predetermined period of time.

8. An emergency medical service demand prediction method for causing a processor to execute computer program instructions and being implemented by an emergency medical service demand prediction device that predicts a quantity of occurrences of emergency medical service requests in a target area, the emergency medical service demand prediction method comprising executing on the processor the steps of:
obtaining actual history data including transport data from an external emergency medical service database, information transmitted from ambulances currently responding to the emergency medical service requests, date/time information indicating dates and times of occurrences of the emergency medical service requests, position information indicating places of the occurrences of the emergency medical service requests, illness/injury information indicating illnesses and injuries that caused the emergency medical service requests, and attribute information of patients including ages and genders;
pre-processing the actual history data by dividing the actual history data into sections, extracting related items, and performing a normalization process to generate:
illness/injury group learning-purpose data used for learning the illnesses and injuries;
prediction model learning-purpose data used for learning a prediction model based on an actual number of the occurrences, the date/time information of each of the illnesses and injuries, and the position information; and
request occurrence number prediction-purpose data used for predicting a quantity of occurrences of future emergency medical service requests;
generating a first learning model, based on the illness/injury group learning-purpose data, including illness/injury groups in which the illnesses and injuries are grouped by a type of the illnesses and injuries by learning occurrence patterns of the illnesses and injuries, and similarities or distances among the illnesses and injuries in association with the dates and times, the position information, and the attribute information of the patients;
generating a second learning model, based on the first leaning model and the prediction model learning-purpose data, including a learned prediction model in which a relationship among a number of occurrences of the illnesses and injuries, the illness/injury groups, the dates and times, and the position information are learned, the learned prediction model indicating an actual number of the occurrences of the emergency medical service requests by the illness/injury groups, unit time, and unit areas in the position information;
predicting the quantity of the occurrences of the future emergency medical service requests in each of the unit areas within the target area based on the second learning model and the request occurrence number prediction-purpose data; and
outputting the predicted quantity of the occurrences of the future emergency medical service requests to an external device.

9. The emergency medical service demand prediction method according to claim 8, further comprising:
obtaining environment data including information related to meteorology of the places of the occurrences of the emergency medical service requests;
generating the second learning model by further receiving an input of the environment data; and
predicting the quantity of the occurrences of the future emergency medical service requests for each of the unit areas, by further inputting the environment data to the second learning model having been trained.

10. The emergency medical service demand prediction method according to claim 8, further comprising:
obtaining region data including information related to a regional statistic of the places of the occurrences of the emergency medical service requests;
generating the second learning model by further receiving an input of the region data; and
predicting the quantity of the occurrences of the future emergency medical service requests for each of the unit areas, by further inputting the region data to the second learning model having been trained.

11. The emergency medical service demand prediction method according to claim 8, further comprising:
obtaining region data including information related to a regional statistic of the places of the occurrences of the emergency medical service requests;
generating a third learning model which receives an input of the region data and output a regional feature value for each of the unit areas;
generating the second learning model by further receiving an input of the regional feature value output from the third learning model; and
predicting the quantity of the occurrences of the future emergency medical service requests for each of the unit areas by further inputting the regional feature value output from the third learning model having been trained, to the second learning model having been trained.

12. The emergency medical service demand prediction method according to claim 8, wherein
the first learning model is structured by using a first layer of a neural network, and
the second learning model is structured by using a second layer of the neural network that receives an output of the first layer as an input.

13. The emergency medical service demand prediction method according to claim 8, further comprising:
determining whether the predicted quantity of the occurrences of the future emergency medical service requests deviates an actual quantity of the occurrences of the future emergency medical service requests in each of the unit areas within the target area in the future for a predetermined period of time; and
performing a re-learn process in which the obtaining of the actual history data, the pre-processing of the actual history data, the generating the first learning model, the generating the second learning model, the predicting of the quantity of the occurrences of the future emergency medical service requests, and the outputting the predicted quantity of the occurrences of the future emergency medical service requests are repeated when the processor determines that the predicted quantity of the occurrences of the future emergency medical service requests deviates the actual quantity of the occurrences of the future emergency medical service requests in each of the unit areas within the target area in the future for the predetermined period of time.

14. A non-transitory computer-readable medium storing computer program instructions for causing a computer to execute a process by a processor so as to perform the steps of:
obtaining actual history data including transport data from an external emergency medical service database, information transmitted from ambulances currently responding to emergency medical service requests, date/time information indicating dates and times of occurrences of the emergency medical service requests, position information indicating places of the occurrences of the emergency medical service requests, illness/injury information indicating illnesses and injuries that caused the emergency medical service requests, and attribute information of patients including ages and genders;
pre-processing the actual history data by dividing the actual history data into sections, extracting related items, and performing a normalization process to generate:
illness/injury group learning-purpose data used for learning the illnesses and injuries;
prediction model learning-purpose data used for learning a prediction model based on an actual number of the occurrences, the date/time information of each of the illnesses and injuries, and the position information; and
request occurrence number prediction-purpose data used for predicting a quantity of occurrences of future emergency medical service requests;
generating a first learning model, based on the illness/injury group learning-purpose data, including illness/injury groups in which the illnesses and injuries are grouped by a type of the illnesses and injuries by learning occurrence patterns of the illnesses and injuries, and similarities or distances among the illnesses and injuries in association with the dates and times, the position information, and the attribute information of the patients;
generating a second learning model, based on the first leaning model and the prediction model learning-purpose data, including a learned prediction model in which a relationship among a number of occurrences of the illnesses and injuries, the illness/injury groups, the dates and times, and the position information are learned, the learned prediction model indicating an actual number of the occurrences of the emergency medical service requests by the illness/injury groups, unit time, and unit areas in the position information within a target area;
predicting the quantity of the occurrences of the future emergency medical service requests in each of the unit areas within the target area based on the second learning model and the request occurrence number prediction-purpose data; and
outputting the predicted quantity of the occurrences of the future emergency medical service requests to an external device.

15. The non-transitory computer-readable medium according to claim 14, further comprising:
obtaining environment data including information related to meteorology of the places of the occurrences of the emergency medical service requests;
generating the second learning model by further receiving an input of the environment data; and
predicting the quantity of the occurrences of the future emergency medical service requests for each of the unit areas, by further inputting the environment data to the second learning model having been trained.

16. The non-transitory computer-readable medium according to claim 14, further comprising:
obtaining region data including information related to a regional statistic of the places of the occurrences of the emergency medical service requests;
generating the second learning model by further receiving an input of the region data; and
predicting the quantity of the occurrences of the future emergency medical service requests for each of the unit areas, by further inputting the region data to the second learning model having been trained.

17. The non-transitory computer-readable medium according to claim 14, further comprising:
obtaining region data including information related to a regional statistic of the places of the occurrences of the emergency medical service requests;
generating a third learning model which receives an input of the region data and output a regional feature value for each of the unit areas;
generating the second learning model by further receiving an input of the regional feature value output from the third learning model; and
predicting the quantity of the occurrences of the future emergency medical service requests for each of the unit areas by further inputting the regional feature value output from the third learning model having been trained, to the second learning model having been trained.

18. The non-transitory computer-readable medium according to claim 14, wherein
the first learning model is structured by using a first layer of a neural network, and the second learning model is structured by using a second layer of the neural network that receives an output of the first layer as an input.

19. The non-transitory computer-readable medium according to claim 14, further comprising:
   determining whether the predicted quantity of the occurrences of the future emergency medical service requests deviates an actual quantity of the occurrences of the future emergency medical service requests in each of the unit areas within the target area in the future for a predetermined period of time; and
   performing a re-learn process in which the obtaining of the actual history data, the pre-processing of the actual history data, the generating the first learning model, the generating the second learning model, the predicting of the quantity of the occurrences of the future emergency medical service requests, and the outputting the predicted quantity of the occurrences of the future emergency medical service requests are repeated when the processor determines that the predicted quantity of the occurrences of the future emergency medical service requests deviates the actual quantity of the occurrences of the future emergency medical service requests in each of the unit areas within the target area in the future for the predetermined period of time.

* * * * *